(12) United States Patent
Cao et al.

(10) Patent No.: US 11,806,001 B2
(45) Date of Patent: Nov. 7, 2023

(54) LOCALIZED FUSION OF NATIVE LEAFLETS USING ACTIVATED ADHESIVE

(71) Applicant: Edwards Lifesciences Corporation, Irvine, CA (US)

(72) Inventors: Hengchu Cao, Irvine, CA (US); Shih-Hwa Shen, Irvine, CA (US); Holly Kung Jung Hsu, Irvine, CA (US); Krystal Ya-Fong Lai, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 335 days.

(21) Appl. No.: 16/850,950

(22) Filed: Apr. 16, 2020

(65) Prior Publication Data

US 2020/0237357 A1 Jul. 30, 2020

Related U.S. Application Data

(63) Continuation of application No. PCT/US2018/056016, filed on Oct. 16, 2018.
(Continued)

(51) Int. Cl.
*A61B 17/00* (2006.01)
*A61F 2/24* (2006.01)
*A61F 2/90* (2013.01)

(52) U.S. Cl.
CPC ........ *A61B 17/00491* (2013.01); *A61F 2/246* (2013.01); *A61F 2/90* (2013.01);
(Continued)

(58) Field of Classification Search
CPC ...... A61B 2017/0065; A61B 17/00491; A61B 2017/00522; A61B 2017/005;
(Continued)

(56) References Cited

U.S. PATENT DOCUMENTS 5,928,611 A * 7/1999 Leung ................. B05D 1/26
422/131
6,428,234 B1 * 8/2002 Bobo ............... A61B 17/00491
401/265

(Continued)

FOREIGN PATENT DOCUMENTS

WO WO-2014110460 A1 * 7/2014 ....... A61B 17/00491

*Primary Examiner* — Timothy J Neal
*Assistant Examiner* — Mitchell Brian Hoag
(74) *Attorney, Agent, or Firm* — KPPB LLP

(57) ABSTRACT

Disclosed is a delivery device, kit, system, method, etc. for localized fusion of leaflets of a tissue valve, for example, a native heart valve, using an adhesive. The delivery device can have one or more capture features for capturing separate leaflets, for example, the anterior and posterior mitral leaflets. An applicator can be configured to apply a biocompatible adhesive between the captured leaflets, and one or more curing elements can be configured to cure the applied biocompatible adhesive. The kit can have the aforementioned delivery device, and the biocompatible adhesive used therewith. The method can include positioning the aforementioned delivery device adjacent the anterior and posterior mitral leaflets, capturing the mitral leaflets between the paddles of the delivery device, applying a biocompatible adhesive between the captured mitral leaflets via the applicator, and curing the applied biocompatible adhesive via the energy elements to locally fuse the mitral leaflets.

18 Claims, 26 Drawing Sheets

Related U.S. Application Data

(60) Provisional application No. 62/575,252, filed on Oct. 20, 2017.

(52) U.S. Cl.
CPC .............. *A61B 2017/005* (2013.01); *A61B 2017/00243* (2013.01); *A61B 2017/00495* (2013.01); *A61B 2017/00522* (2013.01); *A61B 2017/00557* (2013.01); *A61F 2/2442* (2013.01); *A61F 2/2445* (2013.01); *A61F 2/2466* (2013.01); *A61F 2250/0059* (2013.01)

(58) Field of Classification Search
CPC .......... A61B 2017/00495; A61B 2017/00243; A61B 17/12181–12195; A61L 24/00–12; A61F 2/2442–2466
See application file for complete search history.

(56) References Cited

U.S. PATENT DOCUMENTS

| | | | |
|---|---|---|---|
| 7,704,269 B2 | 4/2010 | St. Goar et al. | |
| 7,758,596 B2 | 7/2010 | Oz et al. | |
| 8,323,336 B2 | 12/2012 | Hill et al. | |
| 10,507,108 B2 * | 12/2019 | Delgado | A61B 17/00234 |
| 10,507,109 B2 * | 12/2019 | Metchik | A61F 2/2466 |
| 10,524,792 B2 * | 1/2020 | Hernandez | A61F 2/2463 |
| 11,051,940 B2 * | 7/2021 | Metchik | A61F 2/2466 |
| 2007/0118154 A1 | 5/2007 | Crabtree | |
| 2009/0136589 A1 * | 5/2009 | Crabtree | A61L 24/02 424/602 |
| 2013/0066341 A1 * | 3/2013 | Ketai | A61F 2/246 606/151 |
| 2013/0108352 A1 * | 5/2013 | Ruiz, Sr. | B65D 35/36 401/132 |
| 2014/0348896 A1 * | 11/2014 | Karp | A61L 15/26 525/445 |
| 2016/0192911 A1 * | 7/2016 | Kassab | A61B 1/00165 606/200 |
| 2016/0287383 A1 | 10/2016 | Rowe | |
| 2018/0021134 A1 * | 1/2018 | McNiven | A61F 2/246 623/2.11 |
| 2018/0168803 A1 * | 6/2018 | Pesce | A61F 2/2409 |
| 2018/0243086 A1 * | 8/2018 | Barbarino | A61F 2/2463 |
| 2019/0069991 A1 * | 3/2019 | Metchik | A61F 2/2466 |
| 2019/0099170 A1 * | 4/2019 | Russo | B05D 1/26 |
| 2019/0336136 A1 * | 11/2019 | Kassab | A61B 17/12177 |

* cited by examiner

LOCALIZED FUSION OF NATIVE LEAFLETS USING ACTIVATED ADHESIVE

CROSS-REFERENCES TO RELATED APPLICATIONS

The present application is a continuation of International Patent Application No. PCT/US2018/056016, filed Oct. 16, 2018, which claims priority from U.S. Provisional Patent Application No. 62/575,252 to Cao et al., filed Oct. 20, 2017, and entitled "Localized Fusion of Native Leaflets Using Activated Adhesive," both of which are incorporated herein by reference in their entirety for all purposes.

FIELD OF THE INVENTION

This invention relates generally to devices, systems, and methods for heart valve repair, including to the repair of native leaflets using biocompatible surgical glues and/or adhesives.

BACKGROUND

There is a need for safe and effective devices, systems, techniques, and methods, for the correction of valvular regurgitation. A percutaneous method for treating valvular regurgitation (e.g., mitral valve regurgitation, tricuspid valve regurgitation, etc.) may include deploying a clip or other device to hold ends of native leaflets together. A catheter may be advanced into a chamber of the heart and a clip or other device can be used to draw the leaflets together and/or hold them together or in a fixed relationship relative to each other If a clip or other device it used, then once it is deployed, it will likely have to remain inside the patient as an implant. Further, the introduction of a foreign object or metallic body into the cardiac system can create risk for tissue damage due to mechanical gripping, device dislodgement, or other damage to surrounding structures.

SUMMARY

This summary is meant to provide some examples and is not intended to be limiting of the scope of the invention in any way. For example, any feature included in an example of this summary is not required by the claims, unless the claims explicitly recite the features. Also, the features described can be combined in a variety of ways. The description herein relates to systems, assemblies, methods, devices, apparatuses, combinations, kits, techniques, etc. for the localized fusion of valve leaflets (e.g., mitral, tricuspid, aortic, and/or pulmonary valve leaflets) using an adhesive to restore or improve valve function. Beneficially, the need for a permanent implant (e.g., metallic device, clip, spacer, etc.) can be eliminated in many instances. Various features and steps as described elsewhere in this disclosure may be included in the examples summarized here.

A delivery device or system for application of an adhesive between valve leaflets (e.g., a first leaflet and a second leaflet; an anterior leaflet and a posterior leaflet; a first leaflet, a second leaflet, and a third leaflet; etc.) of a tissue valve (e.g., valve including tissue leaflets, native heart valve, etc.) can be provided for localized fusion of the valve leaflets.

The delivery device or system can comprise a capture feature or multiple capture features or capture means for capturing the valve leaflets (e.g., a first leaflet and a second leaflet; an anterior leaflet and a posterior leaflet of a mitral valve; a first leaflet, a second leaflet, and a third leaflet; etc.) separately and/or collectively. One or more other capture features and/or other features/components of these described elsewhere in this disclosure can also or alternatively be used or included.

Optionally, the capture feature(s) can comprise one or more paddles (e.g., a pair of opposing paddles, three paddles, more, etc.). The paddles can be configured such that each paddle can articulate between an open and closed configuration separately and/or together to capture the leaflets (e.g., one or more of the anterior leaflet, posterior leaflet, first leaflet, second leaflet, third leaflet, etc.).

Optionally, the capture feature(s) can comprise one or more clips (e.g., a pair of clips, at least four steerable clips, more clips, etc.). The clips or a subset of the clips (e.g., at least two clips) can be configured to capture a first leaflet (e.g., the anterior mitral leaflet), the clips or another subset of the clips (e.g., at least two other clips) can be configured to capture a second leaflet (e.g., the posterior mitral leaflet), and/or the clips or another subset of the clips can be configured to capture another leaflet.

The delivery device or system can include an applicator configured to apply the adhesive between the leaflets (e.g., between a first leaflet and a second leaflet; between the anterior leaflet and the posterior leaflet of a mitral valve; between a first leaflet, a second leaflet, and a third leaflet; etc.). One or more other applicators, adhesives, and/or other features/components of these described elsewhere in this disclosure can also or alternatively be used or included. For example, the applicator can optionally comprise a porous material through which the adhesive is applied. Further, the applicator can be detachable from the capsule, the applicator can be configured to retract within an interior cavity of the capsule, or both.

The adhesive can be biocompatible. The adhesive can be one of the adhesives listed in this disclosure or have features/characteristics listed in this disclosure. In some embodiments, the adhesive comprises at least one pre-polymer and at least one initiator. Optionally, the at least one pre-polymer can be activated by one or more functional groups that can be reacted to form crosslinks between polymer chains. The at least one pre-polymer can be composed or selected such that it is not activated by biological fluids. In some embodiments, the at least one initiator can be a photoinitiator.

The delivery device or system can also include one or more curing elements or captured anterior and posterior mitral leaflets, and one or more energy elements configured to cure the applied adhesive. The curing elements can be configured to deliver ultraviolet (UV) radiation or other energy to cure the applied adhesive. In one embodiment, at least one of the one or more energy elements is a fiber optic configured to deliver ultraviolet (UV) radiation out of a distal tip thereof.

In one embodiment, a delivery device for application of an adhesive between anterior and posterior mitral leaflets for localized fusion thereof includes one or more capture features for capturing the anterior and posterior mitral leaflets, an applicator configured to apply the adhesive between the captured anterior and posterior mitral leaflets, and one or more energy elements configured to cure the applied adhesive. At least one of the one or more energy elements can be configured to deliver ultraviolet (UV) radiation to cure the applied adhesive. In one embodiment, at least one of the one or more energy elements is a fiber optic configured to deliver ultraviolet (UV) radiation out of a distal tip thereof. The adhesive can be biocompatible.

In one embodiment, the applicator includes a porous material through which the adhesive is applied.

In one embodiment, the adhesive includes at least one pre-polymer and at least one initiator. Where the adhesive includes at least one pre-polymer, the at least one pre-polymer can be activated by one or more functional groups that can be reacted to form crosslinks between polymer chains and where the at least one pre-polymer is not activated by biological fluids. The at least one initiator can be a photoinitiator.

In one embodiment, the one or more capture features includes a pair of opposing paddles, each paddle configured to articulate between an open and closed configuration to capture one of the anterior or posterior mitral leaflets. In one embodiment, the one or more capture features includes an inflatable balloon, where the inflatable balloon captures one of the anterior or posterior mitral leaflets. In one embodiment, the one or more capture features includes at least four steerable clips, where at least two clips are configured to capture the anterior mitral leaflet and at least two clips are configured to capture the posterior mitral leaflet.

In one embodiment, the delivery device further includes a capsule including a first end, a second end, and a side surface extending therebetween, where the applicator and the one or more energy elements are coupled to the first end of the capsule. The one or more energy elements can surround or substantially surround the applicator or be spaced at equidistant locations around the applicator, e.g., such that adjacent energy elements are equidistant from each other and/or from the applicator.

In one embodiment, the applicator is detachable from the capsule. In one embodiment, the applicator is configured to retract within an interior cavity of the capsule.

In one embodiment, the capsule includes at least one interior cavity in fluid communication with the applicator, where the adhesive is stored in the at least one interior cavity prior to being applied between the anterior and posterior mitral leaflets via the applicator.

In one embodiment, the delivery device further includes an arm coupled to the second end of the capsule. Where the delivery device includes an arm, the delivery device can further include an expandable scaffold coupled to at least a portion of the capsule or at least a portion of the arm, where the expandable scaffold is configured to stabilize the delivery device during application of the adhesive between the anterior and posterior mitral leaflets.

In one embodiment, the one or more capture features includes a pair of opposing paddles coupled to at least a portion of the capsule, where each paddle is configured to articulate between an open and closed configuration to capture one of the anterior or posterior mitral leaflets.

In one embodiment, a method for localized fusion of anterior and posterior mitral leaflets via application of a biocompatible adhesive therebetween includes one, some, or all of the following: positioning a delivery device (which can be the same as or similar to the delivery devices described above or in other locations herein) adjacent to the anterior and posterior mitral leaflets of a patient, capturing the anterior and posterior leaflets via the one or more capture features of the delivery device, applying the biocompatible adhesive between the captured anterior and posterior mitral leaflets via the applicator of the delivery device, and curing the applied biocompatible adhesive via the one or more energy elements of the delivery device to locally fuse the anterior and posterior mitral leaflets together. Other steps described elsewhere herein can also be used.

In one embodiment, a delivery device for application of an adhesive between native leaflets for localized fusion thereof includes capture features for capturing the native leaflets, an applicator configured to apply the adhesive between each of the native leaflets when captured by the capture features, and one or more curing elements configured to cure the adhesive after the adhesive has been applied to the native leaflets. At least one of the one or more curing elements can be configured to deliver ultraviolet (UV) radiation to cure the adhesive. At least one of the one or more curing elements can be a fiber optic configured to deliver ultraviolet (UV) radiation out of a distal tip thereof. The adhesive can be biocompatible.

In one embodiment, the applicator includes a porous material through which the adhesive is applied.

In one embodiment, the adhesive includes at least one pre-polymer and at least one initiator. In one embodiment, where the adhesive includes at least one pre-polymer, the at least one pre-polymer can be activated by one or more functional groups that can be reacted to form crosslinks between polymer chains and where the at least one pre-polymer is not activated by biological fluids. In one embodiment, where the adhesive includes at least one initiator, the at least one initiator can be a photoinitiator.

In one embodiment, the capture features include opposing paddles, each paddle configured to articulate between an open and closed configuration to capture one of the native leaflets. In one embodiment, the one or more capture features includes an inflatable balloon, where the inflatable balloon captures one of native leaflets.

In one embodiment, the capture features include at least four steerable clips, where at least two clips are configured to capture a first native leaflet and at least two clips are configured to capture a second native leaflet.

In one embodiment, the delivery device further includes a capsule including a first end, a second end, and a side surface extending therebetween, where the applicator and the one or more curing elements are coupled to the first end of the capsule. The capsule can include one or more interior cavities in fluid communication with the applicator, where the adhesive is stored in the one or more interior cavities prior to being applied between the native leaflets via the applicator.

In one embodiment, the delivery device further includes an arm coupled to the second end of the capsule. Where the delivery device includes an arm, the delivery device can further include an expandable scaffold coupled to at least a portion of the capsule or at least a portion of the arm. The expandable scaffold can be configured to stabilize the delivery device during application of the adhesive between the native leaflets.

In one embodiment, the applicator is detachable from the capsule or another portion or component of the delivery system. In one embodiment, the applicator is configured to retract within an interior cavity of the capsule or an interior cavity of another portion or component of the delivery system.

Where the delivery device includes a capsule, the capture features can include opposing paddles coupled to at least a portion of the capsule. Each paddle can be configured to articulate between an open and closed configuration simultaneously or separately to capture each of the native leaflets.

The capture features can include a balloon, wherein the balloon is inflatable to capture one of the native leaflets.

In one embodiment, the capture features include at least four steerable clips, where at least two clips are configured to capture a first leaflet and at least two clips are configured to capture a second native leaflet.

In one embodiment, the one or more curing elements substantially surround the applicator. The one or more curing elements can be arranged in an equidistant arrangement around the applicator and can each be equidistant from the applicator. Each pair of adjacent curing elements can be equidistant from each other around the applicator.

In one embodiment, a method for localized fusion of native leaflets via application of an adhesive therebetween includes one, some, or all of the following: positioning a delivery device (which can be the same as or similar to delivery devices described above or elsewhere herein) adjacent to native leaflets of a patient, capturing the native leaflets via the capture features of the delivery device, applying the adhesive between the native leaflets via the applicator of the delivery device after capturing the native leaflets, and curing the adhesive via the one or more curing elements of the delivery device to locally fuse the native leaflets together. Other steps described elsewhere herein can also be used.

In one embodiment, a delivery device for application of an adhesive between an anterior leaflet and a posterior leaflet of a native mitral valve for localized fusion thereof includes capture means for capturing the anterior leaflet and the posterior leaflet, an applicator configured to apply the adhesive between the anterior leaflet and the posterior leaflet once captured by the capture means, at least one curing element configured to cure the adhesive after it has been applied between the anterior leaflet and the posterior leaflet. The at least one curing element can be configured to deliver ultraviolet (UV) radiation to cure the adhesive.

The adhesive can include at least one pre-polymer and at least one initiator. Where the adhesive includes at least one pre-polymer, the at least one pre-polymer can be activated by one or more functional groups that can be reacted to form crosslinks between polymer chains. In various embodiments, the at least one pre-polymer is not activated by biological fluids. The at least one initiator can be a photoinitiator or multiple photoinitiators.

In one embodiment, the capture means includes a pair of opposing paddles. Each paddle can be configured to articulate between an open and closed configuration to separately capture one of the anterior leaflet or the posterior leaflet.

In one embodiment, the capture means includes a pair of balloons. Each balloon of the pair of balloons can be configured to separately capture one of the anterior or posterior mitral leaflets as the balloon inflates.

In one embodiment, the capture means includes multiple clips. At least two clips of the multiple clips can be configured to capture the anterior leaflet and at least two clips of the multiple clips can be configured to capture the posterior leaflet.

In one embodiment, the delivery device further includes a capsule including a first end, a second end, and a side surface extending therebetween. The applicator and the at least one curing element can be coupled to the first end of the capsule.

In one embodiment, the applicator is detachable from other components of the delivery device. In one embodiment, the applicator is retractable within another component of the device.

In one embodiment, the delivery device includes an expandable scaffold. The expandable scaffold can be configured to stabilize the delivery device during application of the adhesive between the anterior leaflet and the posterior leaflet.

In one embodiment, a method for localized fusion of an anterior leaflet and a posterior leaflet of a mitral valve via application of an adhesive therebetween includes positioning a delivery device (which can be the same as or similar to delivery devices described above or elsewhere herein) adjacent to the anterior leaflet and the posterior leaflet of the mitral valve, separately capturing the anterior leaflet and the posterior leaflet of the mitral valve via the capture means of the delivery device, applying the adhesive between the anterior leaflet and the posterior leaflet via the applicator of the delivery device, and after applying the adhesive, curing the adhesive via the at least one curing element of the delivery device to locally fuse the anterior leaflet and the posterior leaflet together. Other steps described elsewhere herein can also be used.

In one embodiment, a delivery device for application of an adhesive between leaflets of a tissue valve for localized fusion thereof includes capture means for capturing at least a first leaflet and a second leaflet of the tissue valve, an applicator configured to apply the adhesive between at least the first leaflet and the second leaflet once captured by the capture means, and at least one energy element configured to cure the adhesive after it has been applied between at least the first leaflet and the second leaflet. The at least one energy element or multiple energy elements can be configured to deliver ultraviolet (UV) radiation to cure the adhesive.

In one embodiment, the adhesive includes at least one pre-polymer and at least one initiator. The at least one pre-polymer can be activated by one or more functional groups that can be reacted to form crosslinks between polymer chains. In one embodiment, the at least one pre-polymer is not activated by biological fluids. The at least one initiator can be a photoinitiator or multiple photoinitiators.

In one embodiment, the capture means includes a pair of opposing paddles. Each paddle can be configured to articulate between an open and closed configuration to separately capture the first leaflet or the second leaflet.

In one embodiment, the capture means includes a pair of balloons. Each balloon can be configured to inflate to capture one of the first leaflet or the second leaflet.

In one embodiment, the capture means includes multiple clips. At least two clips of the multiple clips can be configured to capture the first leaflet and at least two clips of the multiple clips can be configured to capture the second leaflet.

In one embodiment, the delivery device further includes a capsule including a first end, a second end, and a side surface extending therebetween. The applicator and the at least one energy element can be coupled to the first end of the capsule.

In one embodiment, the applicator is detachable from other components of the delivery device, e.g., the capsule, etc. In one embodiment, the applicator is configured to retract within another component of the delivery device, e.g., within the capsule, etc.

In one embodiment, the delivery device further includes an expandable scaffold. The expandable scaffold can be configured to stabilize the delivery device during application of the adhesive between at least the first leaflet and the second leaflet.

The devices and systems described above can include additional components described elsewhere herein.

In one embodiment, a method for localized fusion of leaflets of a tissue valve or heart valve via application of an adhesive therebetween includes positioning a delivery device (which can be the same as or similar to delivery devices described above or elsewhere herein) adjacent to at least a first leaflet and a second leaflet of the tissue valve or heart valve, separately capturing the first leaflet and the second leaflet via the capture means of the delivery device, applying the adhesive between at least the first leaflet and the second leaflet via the applicator of the delivery device, and after applying the adhesive, curing the adhesive via the at least one energy element of the delivery device to locally fuse at least the first leaflet and the second leaflet together. Other steps described elsewhere herein can also be used.

Various methods are also described herein that involve applying an adhesive to leaflets of a tissue valve and various associated or additional steps. For example, methods for localized fusion of leaflets via application of an adhesive (e.g., a biocompatible adhesive, etc.) therebetween can comprise positioning a delivery device adjacent the leaflets (e.g., adjacent the anterior and posterior mitral leaflets, etc.) of a valve (tissue valve, heart valve, etc.). The methods can comprise capturing the leaflets (e.g., capturing the anterior and posterior leaflets, etc.) via the capture feature(s) of the delivery device. The methods can include applying the adhesive between the leaflets after they have been captured via the applicator of the delivery device. The methods can also include curing the applied adhesive via the one or more curing elements or energy elements of the delivery device to locally fuse the leaflets (e.g., the anterior and posterior mitral leaflets, etc.) together. Any of the delivery devices or systems described in this disclosure can be used. Also, any other steps described elsewhere in this disclosure can also be used.

BRIEF DESCRIPTION OF THE DRAWINGS

Exemplary and non-limiting embodiments of the inventions may be more readily understood by referring to the accompanying drawings, in which.

DETAILED DESCRIPTION

Figure 1A:
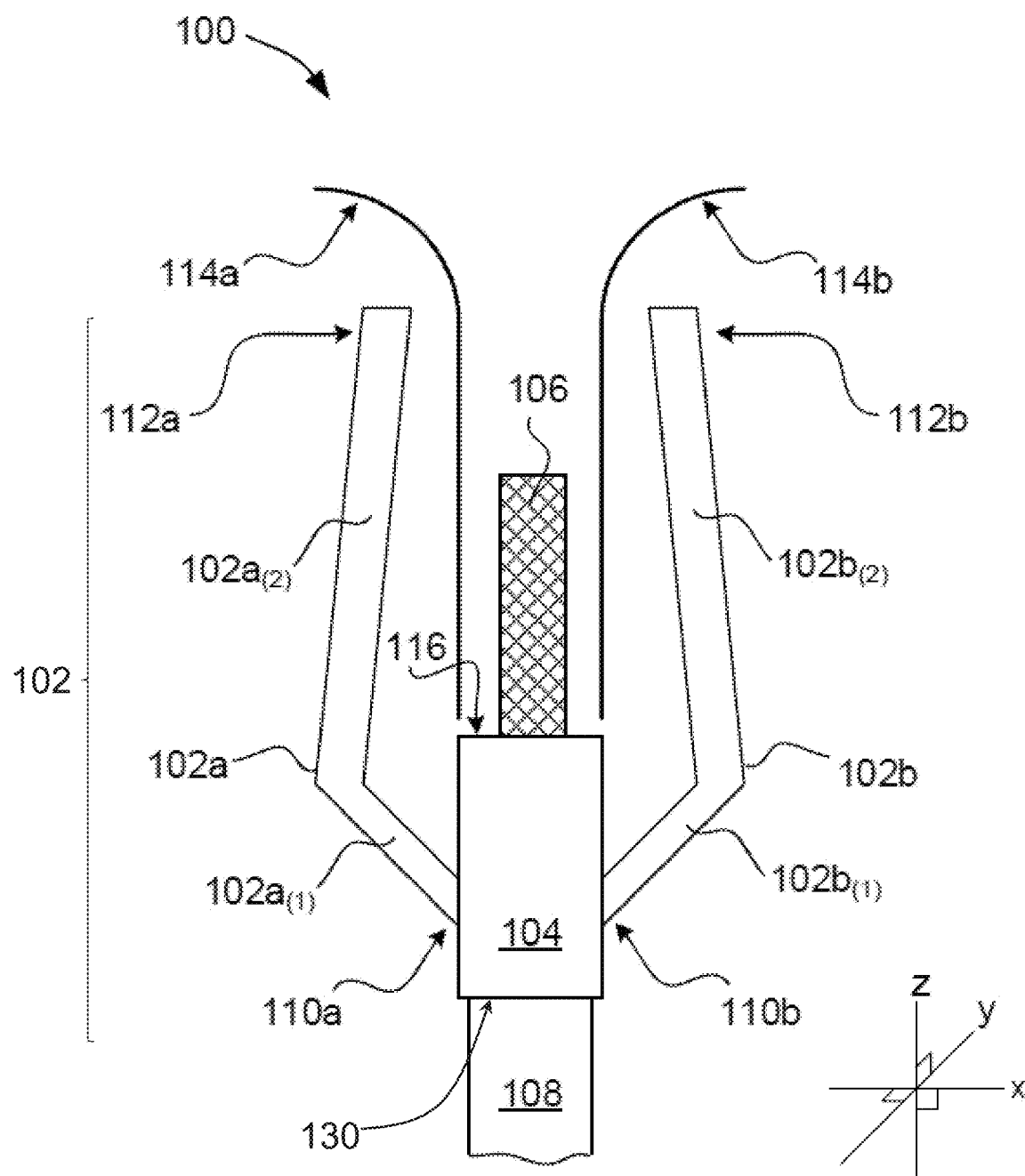
FIGS. 1A-1C and 1D are side and top-down views, respectively, of an exemplary delivery device (e.g., a left ventricular delivery device) for the localized fusion of mitral leaflets via a biocompatible adhesive, according to one embodiment.

The present disclosure provides novel devices, systems, components, features, methods, etc. for correcting or substantially minimizing valvular regurgitation (e.g., mitral regurgitation). For example, the present disclosure provides devices, systems, methods, etc. for correcting or substantially minimizing valvular regurgitation (e.g., mitral regurgitation) via application of a biocompatible adhesive between native leaflets (e.g., between the anterior and posterior leaflets of the mitral valve), and curing said adhesive. Curing can be done by exposure to ultraviolet (UV) radiation, other radiation, heat, or be done in some other way. This biocompatible adhesive can be water-tight, blood resistant, and adhere to wet tissue. Upon curing of this biocompatible adhesive, the leaflets (e.g., mitral leaflets, portions thereof, or other leaflets) are joined together. When mitral leaflets are joined they can form a double orifice configuration, thereby minimizing or reducing mitral valve regurgitation without the use of a permanent implant, device, metallic material, etc.

If a clip or other mechanical device is used to hold the leaflets together, the mechanical device/clip must remain in the cardiac system indefinitely. The biocompatible adhesive used in the devices, systems, methods, etc. described herein nullifies or minimizes the risk of tissue damage due to mechanical gripping or device dislodgement. The biocompatible adhesive can be repositioned to maximize mitral regurgitation mitigation. However, instead of the mechanical repositioning and repeated gripping that might be necessary with a clip or other device, the properties of the biocompatible adhesive can be selectively activated via a curing process (e.g., via exposure to UV radiation) only when the adhesive is positioned as desired on the mitral leaflets, thereby minimizing the risk for tissue damage during adjustment.

Moreover, the exemplary devices for delivery of the biocompatible adhesive, as disclosed herein, can be advanced through the body and to the desired valve in a variety of ways, e.g., through the left atrial or left ventricular cavity, transseptally, transapically, transfemorally, etc. Such delivery devices can thus comprise unique capture means for capturing the anterior or posterior mitral leaflets depending on the delivery/transport route through the heart.

Referring now to FIGS. 1A-1D, an exemplary delivery device 100 for the application of an adhesive between leaflets of a native valve is shown. While delivery device 100 is adapted such that it can be used to apply an adhesive between the posterior and anterior leaflets of a mitral valve and may be described herein with reference to the mitral valve, the invention is not so limited, and the principles, features, etc. can be adapted for and applied to other valves. The delivery device 100 can be advanced through the left ventricular cavity of a patient's heart and/or through other chambers of the heart. The delivery device 100 or components/features thereof can be implemented in combination with, or as an alternative to, other devices/features/components described herein, such as those described with reference to other embodiments and figures. The delivery device 100 can additionally be utilized in any of the methods for making and/or using such devices/components/features described herein. The delivery device 100 can also be used in various applications and/or in permutations, which may or may not be noted in the illustrative embodiments described herein. For instance, the delivery device 100 can include more or less features/components than those shown in FIGS. 1A-1D, in some embodiments. Moreover, the delivery device 100 is not limited to the size, shape, number of components, etc. specifically shown in FIGS. 1A-1D.

As shown in FIGS. 1A-1D, some embodiments of the delivery device 100 comprise a capture feature 102 to capture valve leaflets and drawing and/or moving these leaflets toward each other, a capsule 104, an applicator 106, and an arm 108. As shown in FIGS. 1A-1D, the capture feature 102 can be comprised of paddles (e.g., one, two, three, or more paddles). Although paddles are shown in these figures, the capture features can include other means of drawing and/or moving leaflets toward each other, such as clamps, clips, arms, extensions, attachment portions, inflatable balloons, and/or combinations thereof. In the example shown in FIGS. 1A-1D, the capture feature comprises two paddles 102a, 102b, each of which comprises an attachment portion 110a, 110b that contacts the capsule 104, and an end portion (a "free end" portion) 112a, 112b configured to contact, capture, and move a mitral valve leaflet (e.g., the anterior 114a or posterior 114b mitral leaflet). As discussed in greater detail herein, the pair of paddles 102a, 102b can be configured to contact and capture the mitral leaflets from the outer surface of native leaflets (e.g., the outer or ventricular surface of the anterior and posterior mitral leaflets 114a, 114b).

Figure 1B:
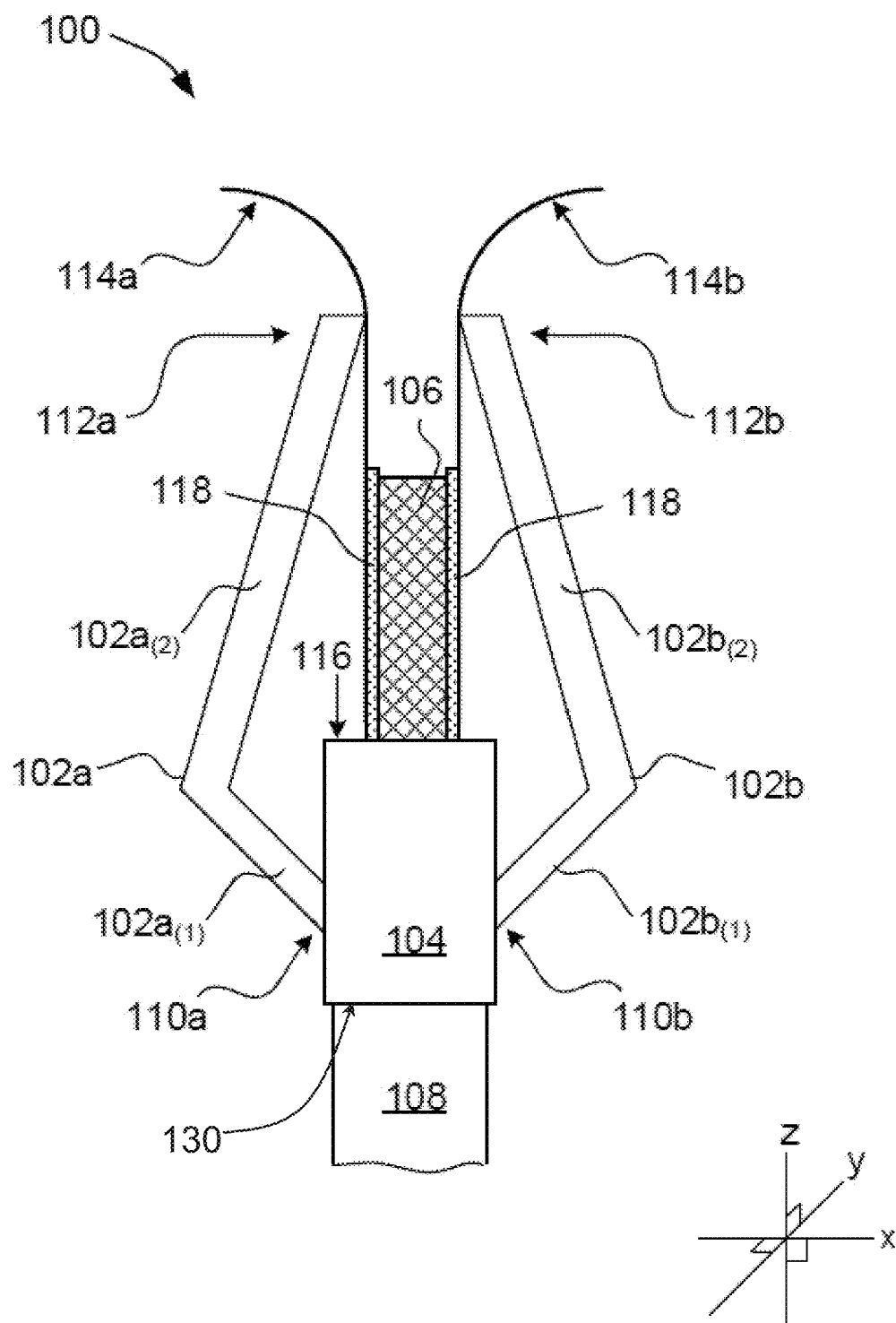

In some embodiments, the capture features or paddles 102a, 102b move from an open configuration (e.g., as illustrated in FIG. 1A) to a closed configuration (e.g., as illustrated in FIG. 1B) and vice versa. In an open configuration (FIG. 1A), the end portions 112a, 112b of the capture features or paddles 102a, 102b can be separated by a first distance. This first distance corresponds to the maximum distance at which the end portions 112a, 112b of the capture features or paddles 102a, 102b can be separated from one another. In some embodiments, separation of the end portions 112a, 112b of the capture features or paddles 102a, 102b by this first distance can result in the capture features or paddles having a generally "V-like" shape or cone-like shape, where the first distance is greater than the distance between attachment portions 110a, 110b. In some embodiments, this first distance can be sufficient to enable the capture features or paddles 102a, 102b to contact and capture native leaflets (e.g., to capture the anterior and posterior mitral leaflets 114a, 114b).

In a closed configuration (FIG. 1B), the end portions 112a, 112b of the capture features or paddles 102a, 102b are closer together, forming a second distance that is less than the aforementioned first distance. This second distance can be the minimum distance at which the end portions 112a, 112b of the capture features or paddles 102a, 102b are separated from one another. In some embodiments, separation of the end portions 112a, 112b of the capture features or paddles 102a, 102b by this second distance can result in the end portions being in contact with, or in close proximity to, one another (e.g., within 1-3 mm).

In some embodiments, the paddles 102a, 102b are in the open configuration (FIG. 1A) when put into contact with native valve leaflets, then moved into the closed configuration (FIG. 1B) to draw and/or move the native leaflets together to apply an adhesive therebetween. For example, the delivery device 100 can be positioned in the left ventricle of the heart with the paddles 102a, 102b in the open configuration (FIG. 1A). The end portions 112a, 112b are placed in contact with the anterior and posterior mitral leaflets 114a, 114b to capture said leaflets (this can be done simultaneously or sequentially one leaflet at a time). The paddles 102a, 102b are then placed in a closed configuration (FIG. 1B) to draw and/or move the mitral leaflets 114a, 114b together to apply an adhesive 118 therebetween.

In instances in which the native leaflets (e.g., the anterior and posterior leaflets 114a, 114b) need to be readjusted with respect to the delivery device 100, the capture features or paddles 102a, 102b can be opened and closed until the optimal position and/or coaptation depth is achieved.

In some embodiments, after application of the adhesive to one or more portions of the captured leaflets (e.g., 114a, 114b), the capture features or paddles 102a, 102b can be moved from the closed to an open configuration and removed from the vicinity of the leaflets 114a, 114b now sealed via the adhesive. Once the capture features or paddles 102a, 102b are no longer within the vicinity of the leaflets 114a, 114b, said capture features or paddles can be moved back to a closed configuration during withdrawal of the delivery device 100 from the heart (e.g., for a lower profile; such a lower profile can also be used during introduction into the body and heart).

Figure 1C:
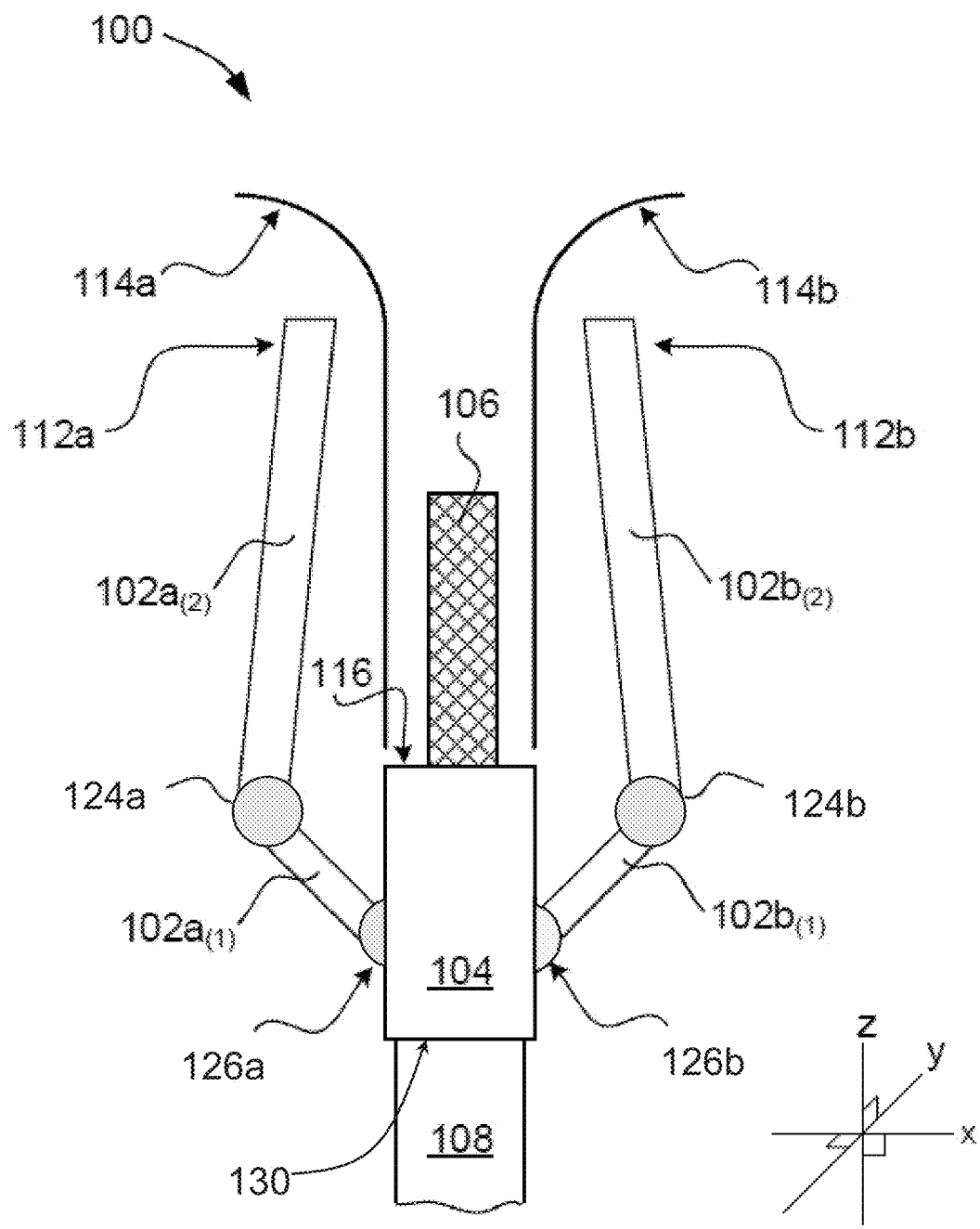
Figure 1D:
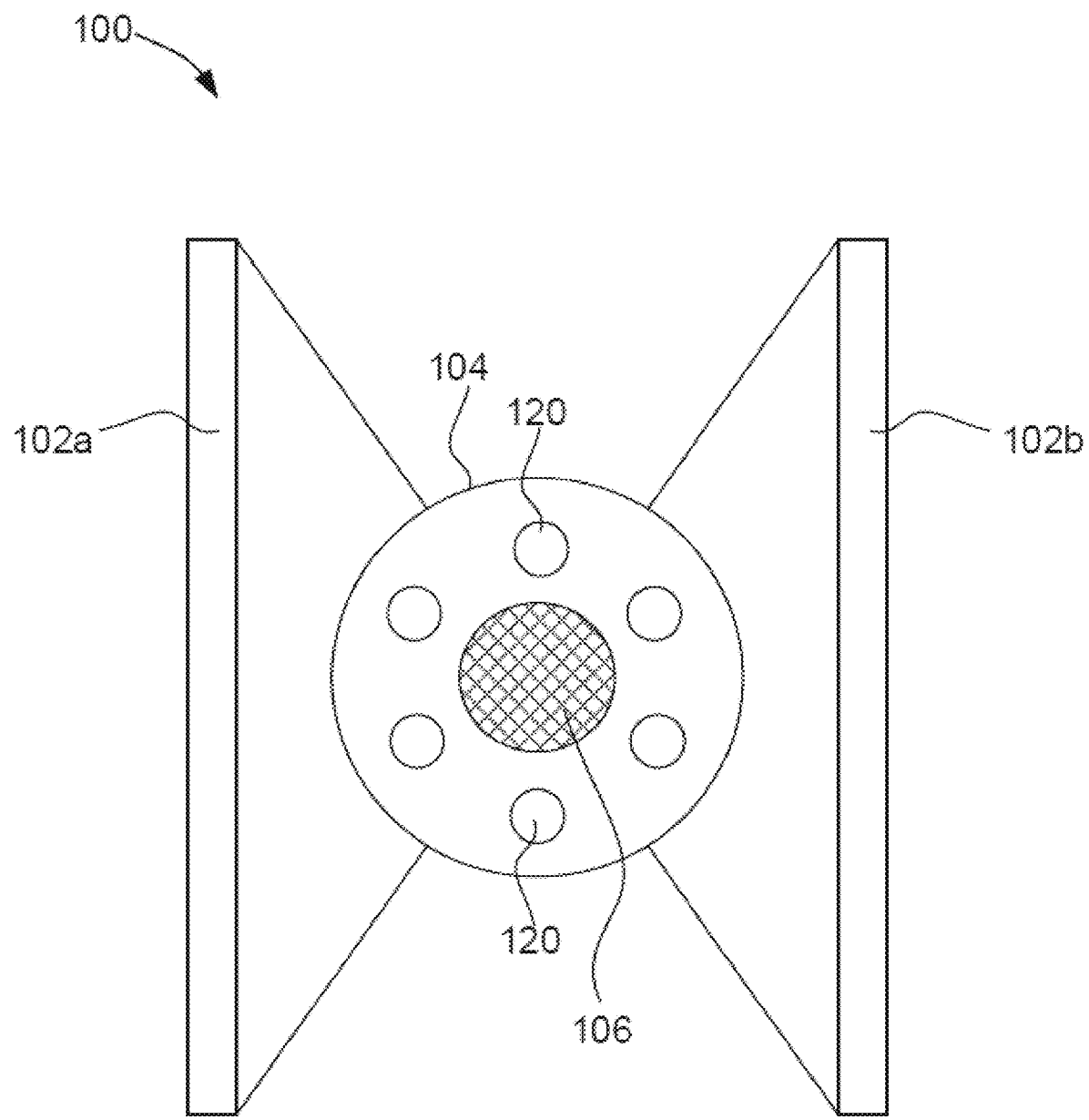
Figure 1D:
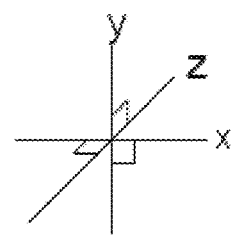

Movement and/or rotation of the capture features (e.g., paddles 102a, 102b) can be achieved via various mechanical means. For instance, each of the capture features or paddles 102a, 102b of some embodiments will comprise at least two different segments oriented at different angles relative to the longitudinal axis of the delivery system 100 (e.g., as measured along the z-axis of FIGS. 1A-1D). As shown in the embodiment of FIGS. 1A-1D, a capture feature or paddle 102a can comprise a first segment $102a_{(1)}$ and a second segment $102a_{(2)}$, where the first segment $102a_{(1)}$ encompasses attachment portion 110a, and the second segment $102a_{(2)}$ encompasses end portion 112a. Likewise, a capture feature or paddle 102b can comprise a first segment $102b_{(1)}$ encompassing attachment portion 110b, and a second segment $102b_{(2)}$ encompassing end portion 112b. In some embodiments, the two segments (e.g., $102a_{(1)}$ and $102a_{(2)}$) of each capture feature or paddle are connected by a joint (FIG. 1C, 124a and 124b). This joint 124a, 124b can allow movement and/or rotation of the second segment $102a_{(2)}$, $102b_{(2)}$ of each capture feature or paddle 102a, 102b relative to the first segment $102a_{(1)}$, $102b_{(1)}$. For example, the joint 124a, 124b of some embodiments will allow the second segment $102a_{(2)}$, $102b_{(2)}$ of each capture feature or paddle 102a, 102b to move in a direction along (or parallel to) the x-axis as shown in FIGS. 1A-1D to transition between the open and closed configurations. In some embodiments, the joint 124a, 124b will allow the second segment $102a_{(2)}$, $102b_{(2)}$ of each capture feature or paddle 102a, 102b to move in a direction along (or parallel to) the y-axis as shown in FIGS. 1A-1D. In some embodiments, the joint 124a, 124b will allow the second segment $102a_{(2)}$, $102b_{(2)}$ of each capture feature or paddle 102a, 102b to rotate a predetermined amount about the z-axis as shown in FIGS. 1A-1D. In some embodiments the joint 124a, 124b will allow the second segment $102a_{(2)}$, $102b_{(2)}$ of each capture feature or paddle 102a, 102b to move along a combination of the x-axis, y-axis, and/or z-axis, as illustrated in FIGS. 1A-1D. These can be combined in various ways.

In some embodiments, each capture feature (e.g., each paddle 102a, 102b) can be comprised of a single, continuous material, which may or may not have one or more different angled segments. Accordingly, some embodiments include a joint (FIG. 1C, 126a and 126b) to couple the attachment portions 110a, 110b of each of the capture features or paddles 102a, 102b to a portion of the delivery device 100 to allow movement and/or rotation of said capture features or paddles 102a, 102b. For example, this joint 126a, 126b can enable each of the capture features or paddles 102a, 102b to move in a direction along (or parallel to) the x-axis as shown in FIGS. 1A-1D to transition between the open and closed configurations; to move in a direction along (or parallel to) the y-axis; and/or to rotate a predetermined amount about the z-axis.

In some embodiments, each capture feature (e.g., each paddle 102a, 102b) is coupled to a portion of the delivery device 100 via a joint (e.g., 126a) to allow movement and rotation of the entire capture feature or paddle, and further comprises at least two segments (e.g., $102a_{(1)}$ and $102a_{(2)}$) coupled by an additional joint (e.g., 124a) to allow movement and/or rotation of a specific segment relative to another segment.

In some embodiments, each capture feature or segments thereof is configured to move independently from other capture features or segments thereof. For example, paddle 102a, or a segment thereof, may move independently from paddle 102b, or a segment thereof. However, in other embodiments, the capture features (e.g., two paddles 102a, 102b), or segments thereof, move in concert such that motion of one of the capture features or paddles, or a segment thereof, causes, results in, and/or is associated with mirrored motion of the other capture feature or paddle, or a segment thereof.

Figure 9:
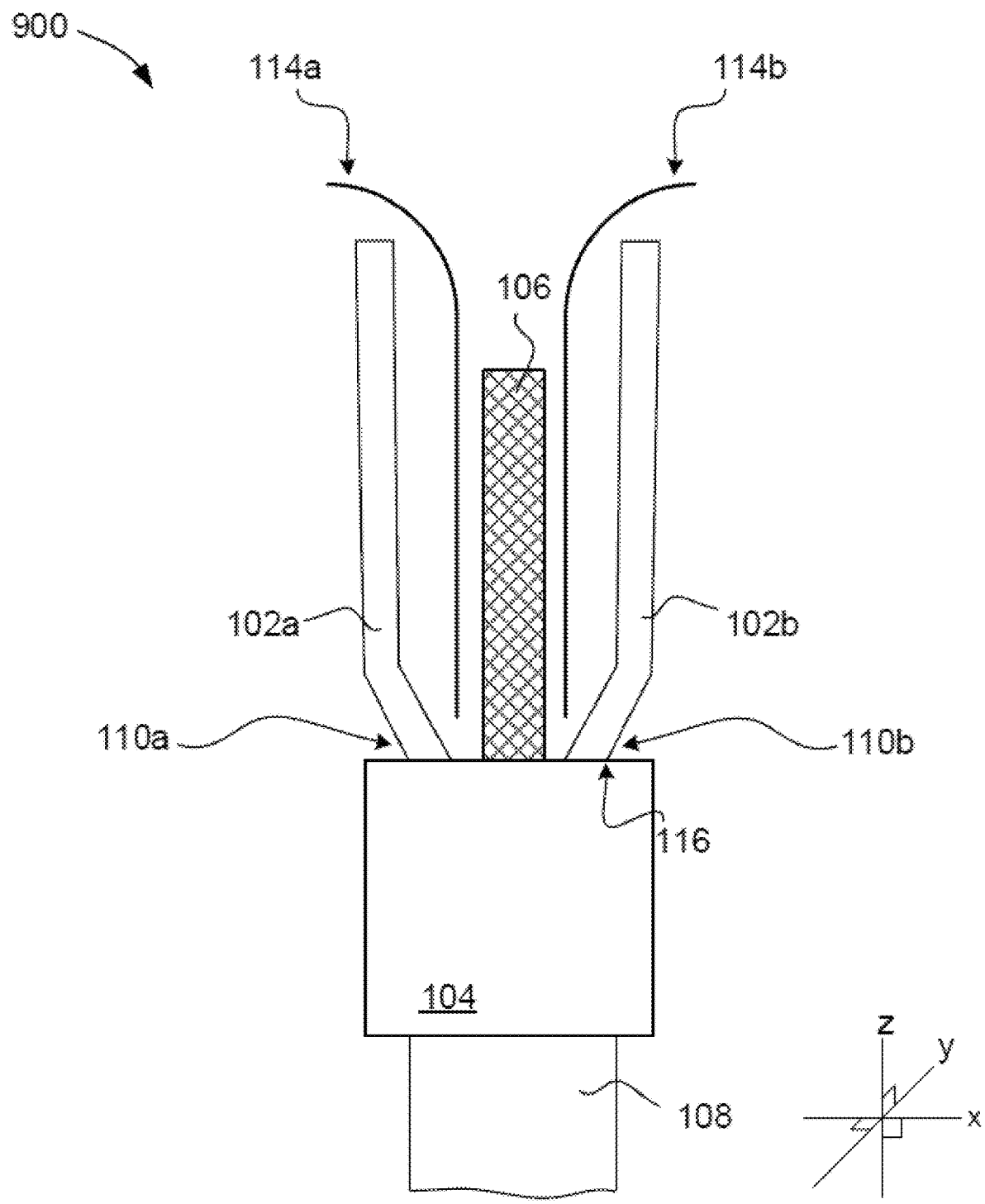
FIG. 9 is a side view of the delivery device of FIGS. 1A-1D illustrating one exemplary design thereof, according to one embodiment.
Figure 10:
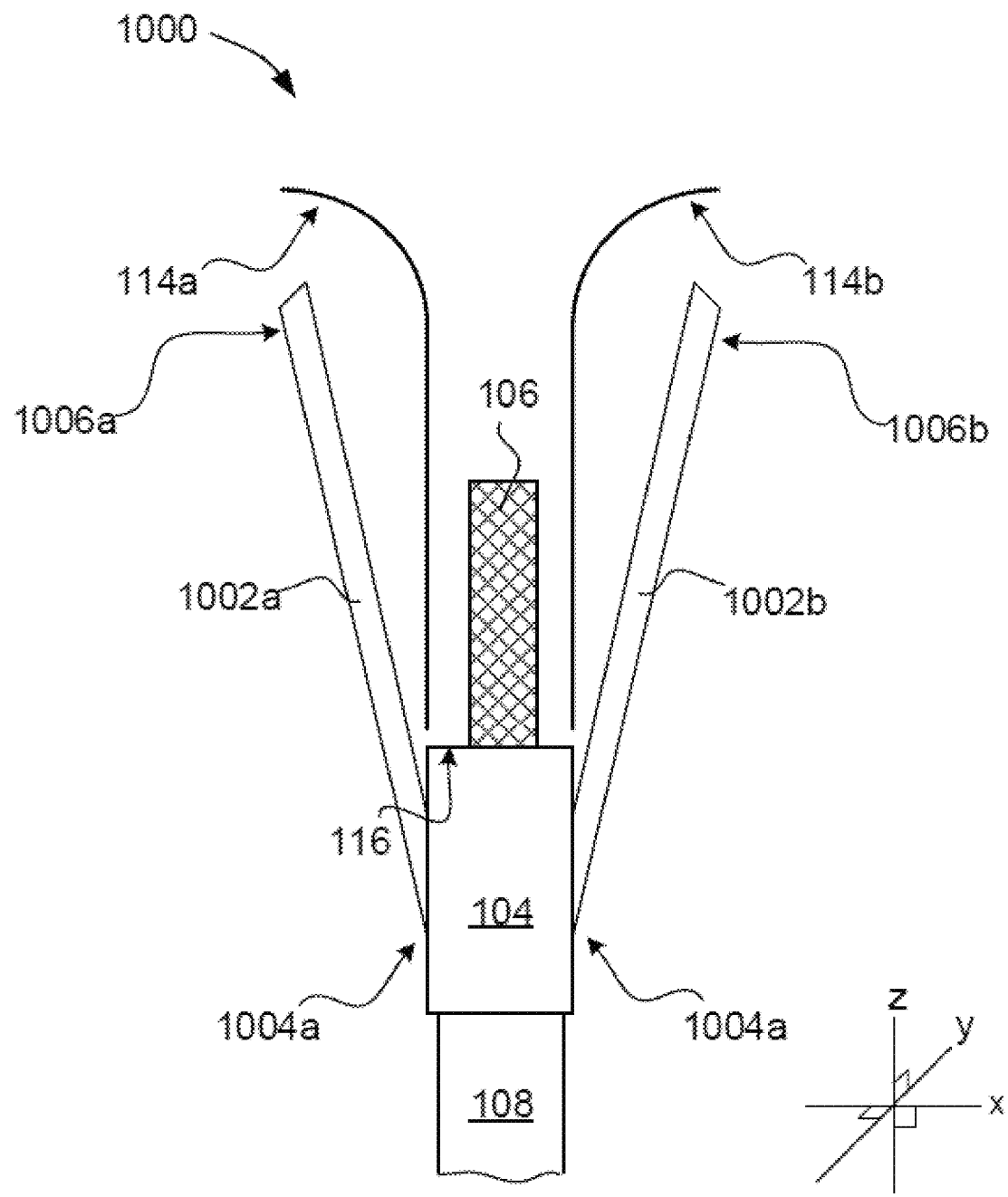
FIG. 10 is a side view of the delivery device of FIGS. 1A-1D illustrating one exemplary design thereof, according to one embodiment.

As shown in the embodiment of FIGS. 1A-1D, the attachment portions 110a, 110b of each of the capture features or paddles 102a, 102b can be coupled to the side surface of the capsule 104. In one embodiment (such as illustrated in FIG. 9), the attachment portions 110a, 110b of each of the capture features or paddles 102a, 102b are coupled to the upper surface (the first end) 116 of the capsule 104, with the applicator 106 positioned therebetween. In one embodiment, the attachment portions 110a, 110b of each of the capture features (e.g., paddles 102a, 102b) is coupled to a portion of the arm 108. Various points of attachment and combinations are possible.

Regardless of the point of attachment to the delivery device 100, each of the capture features (e.g., paddles 102a, 102b) can have dimensions suitable to contact and capture the native leaflets (e.g., the anterior and posterior mitral leaflets 114a, 114b). In some embodiments, each of the capture features (e.g., paddles 102a, 102b) can have a length/height (as measured along the z-axis of FIGS. 1A-1D) in a range from about 2 to about 10 mm; a width (as measured along the y-axis of FIGS. 1A-1D) in a range from about 2 to about 8 mm; and/or a thickness (as measured along the x-axis of FIGS. 1A-1D) in a range from about 0.2 to about 1 mm.

In some embodiments, each of the capture features or paddles 102a, 102b has a uniform or substantially uniform width along its length (e.g., along the z-axis). In other embodiments, each of the capture features or paddles 102a, 102b may not have a uniform width along its length. For instance, in such other embodiments, each of the capture features or paddles 102a, 102b can have a larger width near end portions (e.g., 112a, 112b) as compared to attachment portions (e.g., 110a, 110b), or other portions positioned therebetween. In at least one embodiment, the width of each capture features or paddle 102a, 102b gradually increases from the attachment portions (e.g., 110a, 110b) to the end portions (e.g., 112a, 112b) thereof. In other embodiments, the width of each capture features or paddle 102a, 102b is uniform or substantially uniform along its length but abruptly increases in width near the end portions (e.g., 112a, 112b).

Some embodiments have capture features (e.g., paddles 102a, 102b) constructed of suitable a biocompatible material. Exemplary biocompatible materials for the capture features or paddles 102a, 102b can include, but are not limited to, metal alloys (e.g., Ti alloys such as Ti-6Al-4V; Co—Cr alloys such as Co—Cr—Mo; nitinol; Au alloys; Ag alloys; etc.), stainless steel, plastic materials, polymeric materials, a combination of these, etc. In some embodiments, the capture features or paddles 102a, 102b are constructed of a cloth or a foldable woven mesh.

In some embodiments, as shown in FIGS. 1A-1D, the delivery device 100 includes an applicator 106 protruding from the upper surface (the first end) 116 of the capsule 104. The applicator 106 can be particularly configured to be positioned/inserted between leaflets of a native valve, such as the anterior and posterior leaflets of a mitral valve 114a, 114b, which are captured between the capture features or paddles 102a, 102b. Further, the applicator 106 can be configured to dispense and/or apply an adhesive between the captured leaflets, such as the anterior and posterior mitral leaflets 114a, 114b as illustrated in FIGS. 1A-1C. To that end, the capture features or paddles 102a, 102b can be moved to a closed configuration (e.g., as shown in FIG. 1B) such that sidewalls of the applicator 106 contact and/or are in close proximity to at least a portion of the captured mitral leaflets 114a, 114b, thereby enabling an adhesive 118 to be directly applied to said portions of the leaflets 114a, 114b via the applicator 106. In some embodiments, the adhesive 118 can be applied, via the applicator 106, to the middle segment (e.g., the A2-P2 segment (see FIGS. 18A-18B)) of the mitral leaflets 114a, 114b.

In some embodiments, the applicator 106 is constructed of a porous and/or permeable material through which the adhesive 118 may be applied and/or dispensed. For example, the porous material can be a woven, braided, and/or sponge-like material. In various embodiments, the porous and/or permeable material is pliable and/or compressible, while in other embodiments, the porous and/or permeable material is rigid or partially rigid. The porous and/or permeable material can be biocompatible and/or biodegradable (bioresorbable). For instance, the applicator 106 can comprise a biocompatible and biodegradable (bioresorbable) polymer sponge or cloth bag. Exemplary materials for the applicator 106 include, but are not limited to, fabric, polymeric materials. Further examples of materials that may be used include, but are not limited to, poly(lactic acid) (PLA), poly(lactic-co-glycolic acid), polycaprolactone (PCL), polyhydroxybutyrate (PHB), poly(3-hydroxybutyrate-co-3-hydroxyvalerate (PHBV), polypropylene carbonate (PPC), polybutylene succinate (PBS), polypropylene fumarate (PPF), polyurethane polymers, poly(L-lactide) (PLLA), poly(D-lactide) (PDLA), polyglycolide (PGA), poly(L-lactide-co-glycolide) (PLGA), polyhydroxyalkonate (PHA), polysaccharides, proteins, polyesters, polyhydroxyalkanoates, polyalkelene esters, polyamides, polycaprolactone, polylactide-co-polycaprolactone, polyvinyl esters, polyamide esters, polyvinyl alcohols, modified derivatives of caprolactone polymers, polytrimethylene carbonate, polyacrylates, polyethylene glycol, hydrogels, photo-curable hydrogels, terminal dials, poly (L-lactide-co-trimethylene carbonate), polyhydroxybutyrate; polyhydroxyvalerate, poly orthoesters, poly anhydrides, poly immocarbonates, collagen type I, collagen type III, collagen type IV, collagen VI, collagen XI, collagen XII, fibrillin I, tenascin, decorin, byglycan, versican, asporin, and combinations thereof.

In various embodiments, the applicator 106 maintains a shape and/or dimensions suitable to allow and/or maximize application of the adhesive 118 between the captured valve leaflets (e.g., anterior and posterior mitral leaflets 114a, 114b). In some embodiments, the applicator 106 has a length/height (as measured along the z-axis of FIGS. 1A-1D) that is the same (including substantially the same) as the length/height of the capture features or paddles 102a, 102b. In some embodiments, the applicator 106 has a length/height that is shorter than the length/height of the capture features or paddles 102a, 102b, such as illustrated in FIGS. 1A-1C. For example, the applicator 106 can have a length/height that is about 25% to about 100% of the length/height of the capture features or paddles 102a, 102b. Additionally, in some embodiments, the applicator 106 has a generally circular shape, such as elliptical or ovoid, while other embodiments may possess an applicator 106 with a rectangular, or other cross-sectional shape. It should be noted that in embodiments in which the applicator 106 comprises a pliable and/or compressible material, the shape of the applicator 106 can adjust to conform with the shape of the adjacent portions of the captured leaflets (e.g., 114a, 114b).

Suitable adhesives will comprise one or more (e.g., some or all) of the following characteristics: (1) the adhesive has a sufficient viscosity such that it withstands the hemodynamic forces and resists being washed off the site of application; (2) the adhesive is not reactive with bodily fluids (e.g., blood) and/or does not crosslink in the presence of bodily fluids without exposure to at least one external stimulus; (3) the adhesive is hydrophobic to prevent dilution with aqueous solutions; (4) the adhesive is capable of adhering to wet tissue; (5) the adhesive is biocompatible; and (6) the adhesive is biodegradable.

Biodegradability of the adhesive can be an advantageous characteristic, as it will allow the slow degradation of the adhesive as to limit the amount of foreign particulates in the body. Permanent and foreign matters left in the body have the potential to cause harm, illness, inflammation, or other adverse effects as time proceeds. Adhesives may result in similar reactions within the body, as an adhesive could detach and migrate elsewhere within the circulatory system or even cause an immune reaction within the body. A strategy to prevent possible, long-term effects is to utilize a biodegradable adhesive. Biodegradable adhesives can secure the leaflets for a sufficient time that tissue regenerative processes will permanently fuse the leaflets. After the leaflets are permanently fused by native processes, the adhesive no longer plays a role in securing the leaflets. As such, a suitable biodegradable adhesive will secure leaflets securely for a long enough time that the tissue fusion occurs. After biodegradation, the adhesive—a foreign material—has disappeared, completely or substantially, and will prevent or limit long-term adverse effects.

Adhesives suitable for use in connection with the delivery devices described herein can comprise a crosslinking pre-polymer and an initiator. Exemplary adhesives that can be used in connection with the delivery devices disclosed herein are described in U.S. Patent Application Publication No. 2014/0348896, published Nov. 27, 2014; U.S. Pat. No. 9,006,182, issued Apr. 14, 2015; Lang et al., "A Blood Resistant Surgical Glue for Minimally Invasive Repair of Vessels and Heart Defects, Sci. Transl. Med., 2014, 6(218), 1-20; and Khadem et al., "Healing of Perforating Rat Corneal Incisions Closed With Photodynamic Laser-Activated Tissue Glue," Lasers Surg. Med. 2004, 35(4), 304-311; the entire contents of which are incorporated herein by reference.

In some embodiments, adhesives will comprise one or more pre-polymers. The pre-polymer(s) can be activated by introduction of one or more functional groups (i.e., incorporated on the pre-polymer backbone) that can be reacted to form crosslinks between polymer chains. The functional groups can be selected from the group consisting of: substituted vinyl groups, unsubstituted vinyl groups, substituted acrylate groups, unsubstituted acrylate groups, vinyl esters, vinyl carbamates, vinyl ketones, vinyl amides, vinyl carbonates, vinyl ether groups, vinyl groups in the form of allyl, a combination of these, etc. In one embodiment, the polymer chain is polyester formed from a substituted or unsubstituted polyol, such as a triol, and a substituted or unsubstituted diacid, where the triol can be glycerol. The functional groups can also form crosslinks with the tissue (e.g., native valve or leaflet tissue).

In some embodiments, a pre-polymer will be chosen based on the degree of activation. For example, the degree of activation can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, or 1.5. The degree of activation of the pre-polymer can be within a range between and including any two of the foregoing values. The degree of activation of the pre-polymer can be one of the following: about 0.001, about 0.002, about 0.003, about 0.004, about 0.005, about 0.006, about 0.007, about 0.008, about 0.009, about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1.0, about 1.1, about 1.2, about 1.3, about 1.4, or about 1.5 ("about" being±1 in the lowest decimal place listed for each number).

In some embodiments, the pre-polymer is selected based molecular weight, with higher molecular weight pre-polymers leading to more viscous compositions. For example, the molecular weight can be one of the following values or about/approximately (e.g., ±500 Daltons) one of the following values: 1,000 Daltons, 2,000 Daltons, 3,000 Daltons, 4,000 Daltons, 5,000 Daltons, 6,000 Daltons, 7,000 Daltons, 8,000 Daltons, 9,000 Daltons, 10,000 Daltons, 11,000 Daltons, 12,000 Daltons, 13,000 Daltons, 14,000 Daltons, 15,000 Daltons, 16,000 Daltons, 17,000 Daltons, 18,000 Daltons, 19,000 Daltons, 20,000 Daltons, 21,000 Daltons, 22,000 Daltons, 23,000 Daltons, 24,000 Daltons, 25,000 Daltons, 26,000 Daltons, 27,000 Daltons, 28,000 Daltons, 29,000 Daltons, 30,000 Daltons, 35,000 Daltons, 40,000 Daltons, 45,000 Daltons, 50,000 Daltons, 55,000 Daltons, 60,000 Daltons, 65,000 Daltons, 70,000 Daltons, 75,000 Daltons, 80,000 Daltons, 85,000 Daltons, 90,000 Daltons, 95,000 Daltons, or 100,000 Daltons or more. The molecular weight of the pre-polymer can also be within a range between and including any two of the foregoing values. For example, the molecular weight range may be from about 1,000 Daltons to about 25,000 Daltons.

In some embodiments, pre-polymers are selected based on the absolute viscosity of the pre-polymer. For example, the viscosity of the pre-polymer can be one of the following values or about/approximately (e.g., ±0.5 Pa·s) one of the following values 0.5 Pa·s, 1 Pa·s, 2 Pa·s, 3 Pa·s, 4 Pa·s, 5 Pa·s, 6 Pa·s, 7 Pa·s, 8 Pa·s, 9 Pa·s, 10 Pa·s, 11 Pa·s, 12 Pa·s, 13 Pa·s, 14 Pa·s, 15 Pa·s, 16 Pa·s, 17 Pa·s, 18 Pa·s, 19 Pa·s, 20 Pa·s, 21 Pa·s, 22 Pa·s, 23 Pa·s, 24 Pa·s, 25 Pa·s, 26 Pa·s, 27 Pa·s, 28 Pa·s, 29 Pa·s, 30 Pa·s, 31 Pa·s, 32 Pa·s, 33 Pa·s, 34 Pa·s, 35 Pa·s, 36 Pa·s, 37 Pa·s, 38 Pa·s, 39 Pa·s, 40 Pa·s, 41 Pa·s, 42 Pa·s, 43 Pa·s, 44 Pa·s, 45 Pa·s, 46 Pa·s, 47 Pa·s, 48 Pa·s, 49 Pa·s, 50 Pa·s, 51 Pa·s, 52 Pa·s, 53 Pa·s, 54 Pa·s, 55 Pa·s, 56 Pa·s, 57 Pa·s, 58 Pa·s, 59 Pa·s, 60 Pa·s, 61 Pa·s, 62 Pa·s, 63 Pa·s, 64 Pa·s, 65 Pa·s, 66 Pa·s, 67 Pa·s, 68 Pa·s, 69 Pa·s, 70 Pa·s, 71 Pa·s, 72 Pa·s, 73 Pa·s, 74 Pa·s, 75 Pa·s, 76 Pa·s, 77 Pa·s, 78 Pa·s, 79 Pa·s, 80 Pa·s, 81 Pa·s, 82 Pa·s, 83 Pa·s, 84 Pa·s, 85 Pa·s, 86 Pa·s, 87 Pa·s, 88 Pa·s, 89 Pa·s, 90 Pa·s, 91 Pa·s, 92 Pa·s, 93 Pa·s, 94 Pa·s, 95 Pa·s, 96 Pa·s, 97 Pa·s, 98 Pa·s, 99 Pa·s, or 100 Pa·s. The viscosity can be within a range between and including any two of the foregoing values. For example, in one embodiment, the range for viscosity may be from about 0.5 Pa·s to about 50 Pa·s.

In some embodiments, the pre-polymer is formed by the reaction of a polyol and a polyacid. In one embodiment, the polyol can be one or a combination of compounds comprising two or more hydroxyl groups, including diols, alkane diols, triols, glycerol, trimethylolpropane, triethanolamine, tetraols, erythritol, pentaerythritol, sorbital, unsaturated diols, tetradeca-2,12-diene-1,1,14-diol, macromonomer diols, polyethylene oxide, or N-methyldiethanolamine. In one embodiment, the polyacid can be a diacid or higher order acid and include, for example, glutaric acid, adipic acid, pimelic acid, suberic acid, and azelaic acid. Exemplary long chain acids can include diacids having 5 or more, 10 or more, 15 or more, 20 or more, or 25 or more carbon atoms.

In some embodiments, the pre-polymer is a poly(glycerol sebacate) (PGS) pre-polymer prepared through the polycondensation of equimolar amounts of glycerol and sebacic acid.

In some embodiments, the adhesive also comprises an initiator in combination with the pre-polymer. In some embodiments, the initiator is a photoinitiator, where the photoinitiator is selected from the group consisting of 2-dimethoxy-2-phenyl-acetophenone, 2-hydroxy-1-[4-(hydroxyethoxy)phenyl]-2-methyl-1-propanone (IRGACURE® 2959), 1-hydroxycyclohexyl-1-phenyl ketone (IRGACURE® 184), 2-hydroxy-2-methyl-1-phenyl-1-propanone (DAROCUR® 1173), 2-benzyl-2-(dimethylamino)-1-[4-morpholinyl)phenyl]-1-butanone (Irgacure 369), methylbenzoylformate (DAROCUR® MBF), oxy-phenyl-acetic acid-2-[2-oxo-2-phenyl-acetoxy-ethoxy]-ethyl ester (IRGACURE® 754), 2-methyl-1-[4-(methylthio)phenyl]-2-(4-morpholinyl)-1-propanone (IRGACURE® 907), diphenyl (2,4,6-trimethylbenzoyl)-phosphine oxide (DAROCUR® TPO), phosphine oxide, phenyl bis(2,4,6-trimethyl benzoyl) (IRGACURE® 819), and combinations thereof. In one embodiment, the preferred photoinitiator is IRGACURE® 2959.

In some embodiments, the pre-polymer is stable when exposed to bodily fluids (e.g., blood) and does not spontaneously crosslink in said fluids without exposure to one or more external stimuli such as electromagnetic radiation, heat, a chemical initiator, etc. In one embodiment, the pre-polymer is crosslinked by photopolymerization via exposure to electromagnetic radiation, such as visible or UV light. In these embodiments, the exposure time can be varied in order to achieve the desired amount of crosslinking. In some embodiments, the irradiation time can be 1 second or about 1 second (e.g., ±0.5 second), 5 seconds or about 5 seconds (e.g., ±1 second), 10 seconds or about 10 seconds (e.g., ±2 seconds), 15 seconds or about 15 seconds (e.g., ±2 seconds), 20 seconds or about 20 seconds (e.g., ±3 seconds), 30 seconds or about 30 seconds (e.g., ±3 seconds), 45 seconds or about 45 seconds (e.g., ±4 seconds), one minute or about one minute (e.g., ±5 seconds), 90 seconds or about 90 seconds (e.g., ±5 seconds), or two minutes or about two minutes (e.g., ±10 seconds), or greater. The irradiation time can be in a range between and including any two values of those listed above.

In some embodiments, the intensity of the light is varied as needed to achieve sufficient crosslinking. In one embodiment, the intensity can be less than about 0.45 W/cm$^2$.

In some embodiments, the crosslink density in the cured polymer can be tuned by varying the degree of activation, e.g., acrylation, of the pre-polymer or by varying the curing conditions, such as cure time and the intensity of the energy that is applied to cure the pre-polymer. A greater adhesive strength is believed to be achieved by higher levels of crosslinking.

In some embodiments, the cross-linked polymer can have a crosslinking density of one of the following values or of about/approximately (e.g., ±10% of the amount of the value listed) one of the following values: 0.001%, 0.005%, 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%. The resulting cross-linked polymer can have a crosslinking density within a range of between and including any two of the foregoing values.

In some embodiments, the resulting cross-linked polymer will adhere to wet tissue. For instance, in one embodiment, the cross-linked polymer will have an adhesion strength that is sufficient to secure/join native leaflets together (e.g., the anterior and posterior mitral leaflets 114a, 114b together, for example, near the A2-P2 segment thereof), without the need for additional securing mechanisms such as sutures or staples. In some embodiments, the adhesive strength of the cross-linked polymer is one of the following values or about/approximately (e.g., ±10% of the amount of the value listed) one of the following values: 0.001 N/cm$^2$, 0.002 N/cm$^2$, 0.003 N/cm$^2$, 0.004 N/cm$^2$, 0.005 N/cm$^2$, 0.006

N/cm², 0.007 N/cm², 0.008 N/cm², 0.009 N/cm², 0.01 N/cm², 0.02 N/cm², 0.03 N/cm², 0.04 N/cm², 0.05 N/cm², 0.06 N/cm², 0.07 N/cm², 0.08 N/cm², 0.09 N/cm², 0.1 N/cm², 0.2 N/cm², 0.3 N/cm², 0.4 N/cm², 0.5 N/cm², 0.6 N/cm², 0.7 N/cm², 0.8 N/cm², 0.9 N/cm², 1.0 N/cm², 1.1 N/cm², 1.2 N/cm², 1.3 N/cm², 1.4 N/cm², 1.5 N/cm², 1.6 N/cm², 1.7 N/cm², 1.8 N/cm², 1.9 N/cm², 2.0 N/cm², 2.1 N/cm², 2.2 N/cm², 2.3 N/cm², 2.4 N/cm², 2.5 N/cm², 2.6 N/cm², 2.7 N/cm², 2.8 N/cm², 2.9 N/cm², 3.0 N/cm², 3.5 N/cm², 4.0 N/cm², 4.5 N/cm², 5.0 N/cm², 5.5 N/cm², 6.0 N/cm², 6.5 N/cm², 7.0 N/cm², 7.5 N/cm², 8.0 N/cm², 8.5 N/cm², 9.0 N/cm², 9.5 N/cm², or 10.0 N/cm². The adhesive strength of the cross-linked polymer can be in a range between and including any two of the foregoing values.

With continued reference to FIGS. 1A-1D, the delivery device 100 can additionally comprise one or more energy elements 120 (while described, for example, with respect to energy elements, other types of curing elements can also be used) configured to cure the adhesive dispensed from the applicator 106 and applied at a native heart valve (e.g., between the anterior and posterior mitral leaflets 114a, 114b). In some embodiments, the one or more curing or energy elements 120 can be positioned on one or more portions of the upper surface (the first end) 116 of the capsule 104. In one exemplary embodiment, such as shown in the top down view of FIG. 1D, a plurality of energy elements 120 can be located on the upper surface 116 of the capsule 104, and substantially surround the base of the applicator 106 or be spaced at equidistant locations around the applicator 106. In one embodiment, six energy elements are placed in a circular arrangement around the applicator 106, with each pair of adjacent energy elements equidistant from each other. The configuration and/or number of the curing elements or energy elements 120 is not limited by the embodiment shown in FIG. 1D, and different numbers can be used in similar or different arrangements. The native leaflets or anterior and posterior mitral leaflets 114a, 114b, and the adhesive 118 applied thereto from the applicator 106 are not shown in FIG. 1D for clarity.

In some embodiments, the energy elements 120 will provide thermal energy (e.g., heat), while in other embodiments, the energy elements 120 will provide electromagnetic radiation (e.g., UV or visible light), while in certain other embodiments, the energy elements 120 will provide a combination of both thermal energy and electromagnetic radiation. As one example, all, some, or one of the one or more energy elements 120 can be configured or adapted to provide electromagnetic radiation, such as visible or ultraviolet (UV) light. Similarly, all, some, or one of the one or more energy elements 120 can be configured or adapted to provide visible light (e.g., blue light). In one embodiment, all, some, or one of the one or more energy elements 120 provide UV light.

In embodiments in which at least one of the energy elements 120 provides electromagnetic radiation (e.g., visible or UV light), the angle, θ, at which the electromagnetic radiation is emitted from said energy element relative to a central axis (e.g., the z-axis as shown in FIGS. 1A-1D) can be one of the following values or about/approximately (e.g., ±10% of the amount of the value listed) one of the following values: 0°, ±1°, ±2°, ±3°, ±4°, ±5°, ±6°, ±7°, ±8°, ±9°, ±10°, ±11°, ±12°, ±13°, ±14°, ±15°, ±16°, ±17°, ±18°, ±19°, ±20°, ±22°, ±24°, ±26°, ±28°, ±30°, ±32°, ±34°, ±360, ±38°, ±40°, about ±42°, ±44°, ±46°, ±48°, ±50°, ±52°, ±54°, ±56°, ±58°, ±60°, about ±62°, ±64°, ±66°, ±68°, ±70°, ±72°, ±74°, ±76°, ±78°, ±80°, ±82°, ±84°, ±86°, ±88°, or ±90°. Optionally, the angle θ can be in a range between and including any two of the foregoing values.

In some embodiments in which at least one of the energy elements 120 provides electromagnetic radiation (e.g., visible or UV light), one or more portions of the upper surface 116 of the capsule 104 can comprise one or more of the following: an energy-reflective surface, an energy-reflective coating, a light-reflective surface, and/or a light-reflective coating. In one embodiment, an entirety of the upper surface 116 of the capsule 104 can comprise an energy-reflective surface, an energy-reflective coating, a light-reflective surface, and/or a light-reflective coating.

In some embodiments, the applicator 106 can comprise a porous material, and the porous material of the applicator 106 can be a light transmissive material configured to allow electromagnetic radiation (e.g., visible or UV light) emitted from the one or more energy elements 120 to be incident on the adhesive remaining within the applicator 106. For example, the light transmittance through the porous material of the applicator 106 can be at least 5%, at least 10%, at least 20%, at least 30%, at least 40%, at least 50%, at least 60%, at least 70%, at least 80%, at least 90%, at least 95%, or 100%. Additionally, the light transmittance through the porous material of the applicator 106 can be within a range between and including any two of the foregoing values.

In some embodiments, the applicator 106 is detachable from the capsule 104. In one embodiment, once the capture features or paddles 102a, 102b are moved to a closed configuration and the adhesive 118 is applied in the space between the captured leaflets (e.g., 114a, 114b) via the applicator 106, the one or more curing elements or energy elements 120 can be initiated ("powered on") to cure the applied adhesive 118. After the curing, the delivery device 100 can be withdrawn (e.g., from the heart and further from the body of the patient) and the applicator 106 physically detached from the capsule 104. In some embodiments, the capture features or paddles 102a, 102b can be moved from the closed configuration to an open configuration (or an intermediate configuration therebetween) when the delivery device 100 is withdrawn from the immediate vicinity of the native leaflets or mitral leaflets 114a, 114b. The capture features or paddles 102a, 102b can then be moved back to a closed configuration for a lower profile during withdrawal or further withdrawal of the delivery device 100 from the patient.

Figure 2:
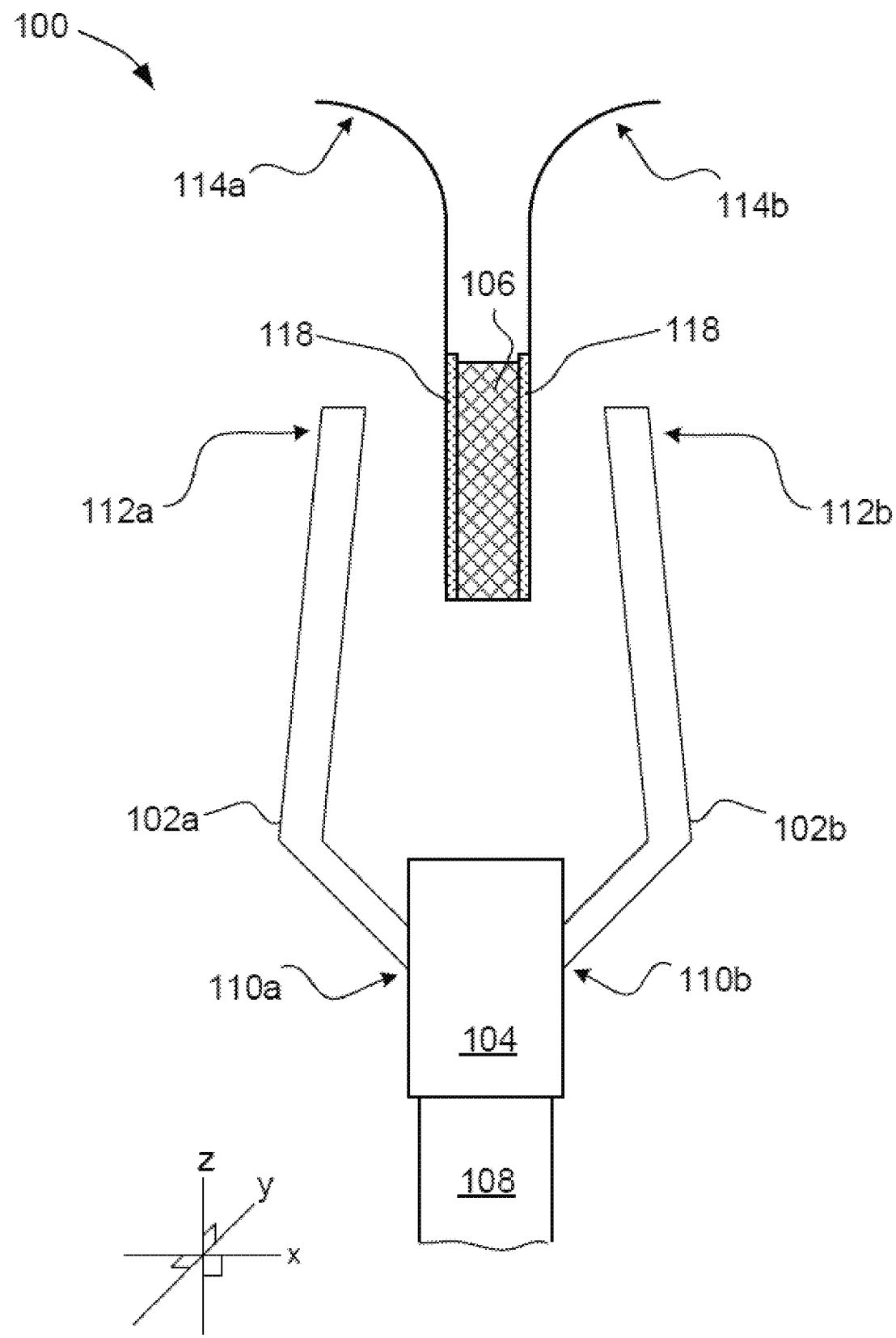
FIG. 2 is a side view of the delivery device of FIGS. 1A-1D, wherein the applicator thereof is detachable, according to one embodiment.

FIG. 2 provides an example in which the delivery device 100 is in the process of withdrawing with the capture features or paddles 102a, 102b in an open configuration, and where the applicator 106 is detached from the capsule 104. In some embodiments, the detached applicator 106 will remain between the native leaflets (e.g., the anterior and posterior mitral leaflets 114a, 114b), after withdrawal of the delivery device 100. In these embodiments, the leaflets are sealed together at least via the cured adhesive 118 located between said leaflets and which can be present on one or more exterior portions and/or the interior portions of the applicator 106 (see FIG. 3).

Figure 3:
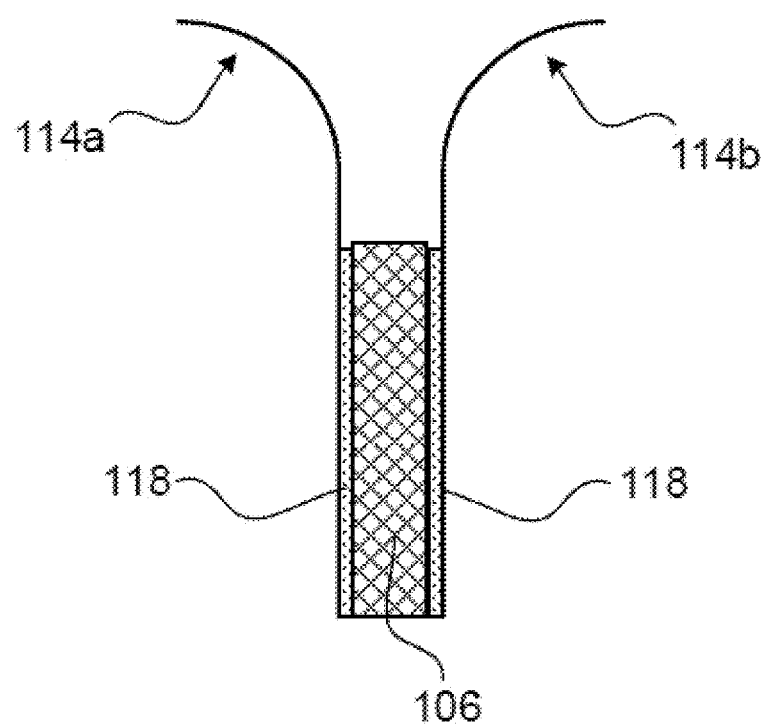
FIG. 3 is a simplified schematic of mitral leaflets that have been fused via use of the delivery device of FIG. 2, wherein the fused mitral leaflets comprise the detached applicator and adhesive present therebetween, according to one embodiment.

In embodiments in which the applicator 106 remains between native leaflets or the mitral leaflets 114a, 114b, as shown in FIG. 3, the applicator 106 will be preferably comprised of a biocompatible material. In some embodiments, the material of the detachable applicator 106 is both biocompatible and biodegradable (e.g., bioresorbable). Degradation (or absorption) of the applicator 106 over time will not affect the integrity of (e.g., will not weaken or otherwise detrimentally affect) the cured adhesive 118 applied between native leaflets or the anterior and posterior mitral leaflets 114a, 114b. For example, the cured adhesive 118 can be present between exterior portions of the applicator 106 and the native leaflets or mitral leaflets 114a, 114b, as well as within the applicator 106. The cured adhesive 118 on the exterior portions of the applicator 106 can thus contact, and be adhered to, the native leaflets or mitral leaflets 114a, 114b. Given that the applicator 106 is preferably comprised of a porous material, the cured adhesive 118 on the exterior portions of the applicator 106 can also be in contact with, and adhered to, the cured adhesive 118 present within the applicator 106. Accordingly, degradation of the porous material of the applicator 106 will not affect the bonding amongst the cured adhesive 118 and which serves to join the native leaflets or mitral leaflets 114a, 114b.

Additionally, in some embodiments with a detachable applicator 106, the applicator will comprise a material to encourage tissue growth and natural fusion of the leaflets (e.g., 114a, 114b). In these embodiments, the material will encourage tissue growth into a scaffold or will comprise a regenerative tissue, which the body will incorporate as its own. Examples of suitable regenerative tissue include, without limitation, decellularized tissue, polyglactin, collagen, and polyglycolic acid. In embodiments using polyglycolic acid scaffolds, the polyglycolic acid scaffolds are bioabsorbable and the extracellular matrix proteins will allow seeding of the host's tissue in order to incorporate the regenerative tissue into the patient's body. Examples of suitable extracellular matrix proteins include, but are not limited to, hydroxyproline, vitronectin, fibronectin and collagen type I, collagen type III, collagen type IV, collagen VI, collagen XI, collagen XII, fibrillin I, tenascin, decorin, byglycan, versican, asporin, and combinations thereof. In some embodiments, polyglycolic acid scaffolds will include the extracellular matrix proteins within the scaffold, while in other embodiments, extracellular matrix proteins will cover the polyglycolic acid scaffolds with extracellular matrix proteins. In yet further embodiments, the extracellular matrix proteins will be both within the polyglycolic acid scaffold and coating the polyglycolic acid scaffolds.

In various embodiments, the applicator 106 and/or adhesive 118 will include tissue growth enhancers or growth factors, which will stimulate or promote the ingrowth of tissue into the applicator 106 or encourage tissue growth for the fusion of valve leaflets (e.g., 114a, 114b). Examples of suitable growth enhancers include but are not limited to, transforming growth factor alpha (TGF-alpha), transforming growth factor beta (TGF-beta), basic fibroblast growth factor (bFGF), vascular epithelial growth factor (VEGF), and combinations thereof. In some embodiments, growth factors are incorporated within the frame material, while some embodiments have the growth factors coating the frame material. In some embodiments, the growth factors are both incorporated in the frame material and coating the frame material. The growth factors can be formulated to release over time or may release as the frame degrades during the bioabsorption process.

In some embodiments, the applicator 106 is configured to retract within an interior cavity of the capsule 104. In one such embodiment, once the capture features or paddles 102a, 102b are moved to a closed configuration and the adhesive 118 is applied in the space between the captured leaflets (e.g., 114a, 114b) via the applicator 106, the applicator 106 can partially or completely retract within the capsule 104.

Figure 4:
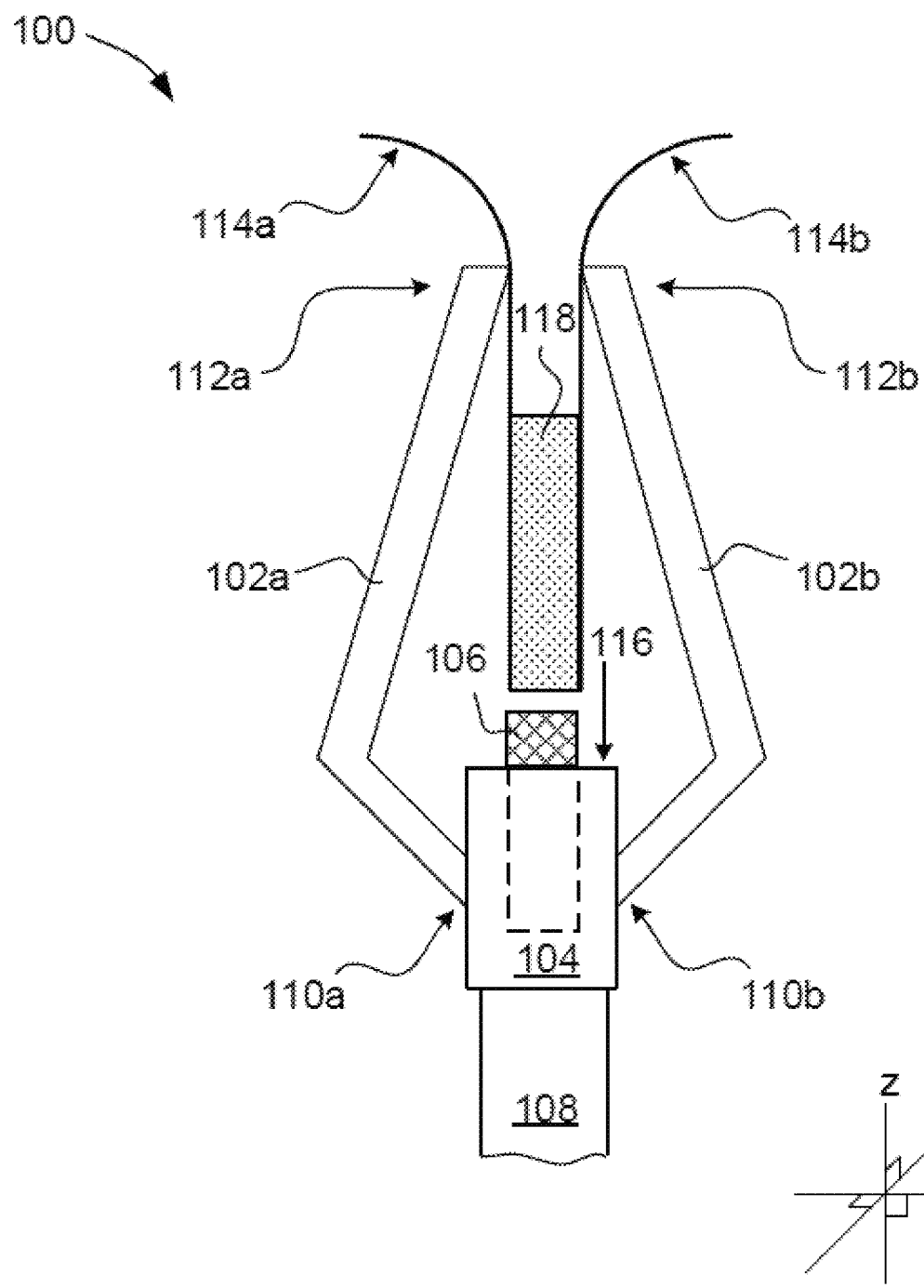
FIG. 4 is side view of the delivery device of FIGS. 1A-1D, wherein the applicator thereof is retractable, according to one embodiment.
Figure 5:
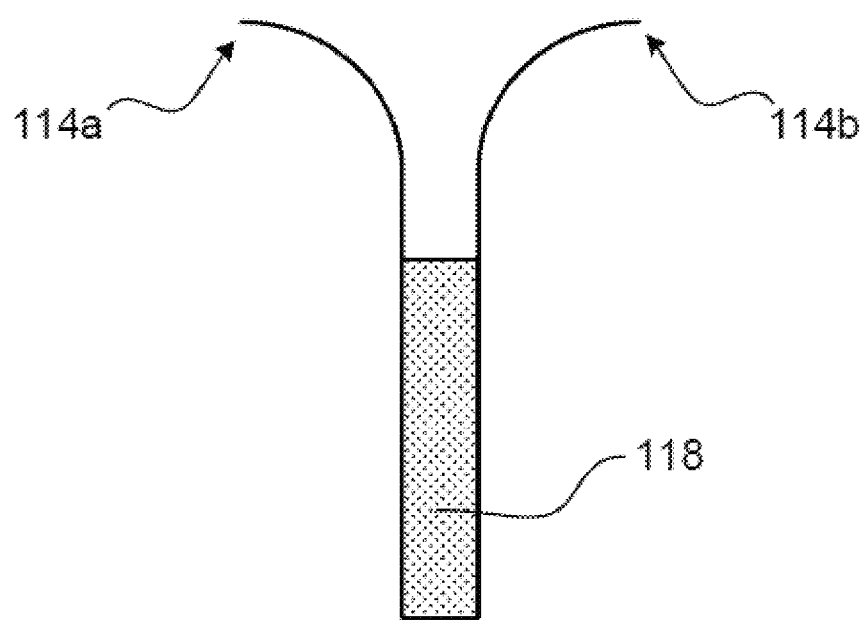
FIG. 5 is a simplified schematic of mitral leaflets that have been fused via use of the delivery device of FIG. 4, wherein the fused mitral leaflets comprise only the biocompatible adhesive present therebetween, according to one embodiment.

FIG. 4 provides an example in which the applicator 106, after dispensing the adhesive 118 between the captured native leaflets or mitral leaflets 114a, 114b, is in the process of retracting within an interior cavity of the capsule 104. After the applicator 106 has partially or completely retracted within the capsule 104, the one or more energy elements 120 can be initiated ("powered on") to cure the applied adhesive 118. After the curing, the delivery device 100 can be withdrawn (e.g., from the heart), thereby leaving the native leaflets (e.g., the anterior and anterior and posterior mitral leaflets 114a, 114b) sealed together via the cured adhesive 118 located between said leaflets (see FIG. 5). In some embodiments, the capture features or paddles 102a, 102b can be moved from the closed configuration to an open configuration (or an intermediate configuration therebetween) when the delivery device 100 is released from and/or withdrawn from the immediate vicinity of the native leaflets or mitral leaflets 114a, 114b. The capture features or paddles 102a, 102b can then be optionally moved back to a closed configuration for further withdrawal of the delivery device 100 from the patient in a lower profile.

With continued reference to FIGS. 1A-1D, the delivery device 100 comprises the arm 108 coupled to a second end 130 of the capsule 104. In some embodiments, the arm 108 can comprise a suitable length that enables the capture features or paddles 102a, 102b to be advanced through a patient's heart (e.g., through the left ventricular cavity) and positioned near the native leaflets (e.g., anterior and posterior mitral leaflets 114a, 114b). The capture features or paddles 102a, 102b are preferably positioned so as to be able to contact and capture the native leaflets at a desired location (e.g., capture the anterior and posterior mitral leaflets 114a, 114b near the middle segment (e.g., the A2-P2 segment)) thereof. Further, in various embodiments, the arm 108 is comprised of a material that is sufficiently rigid to support the capsule 104, applicator tip 106, and the capture features or paddles 102a, 102b, yet sufficiently pliable or flexible to allow the arm 108 to be advanced through certain portions of the heart.

Figure 6:
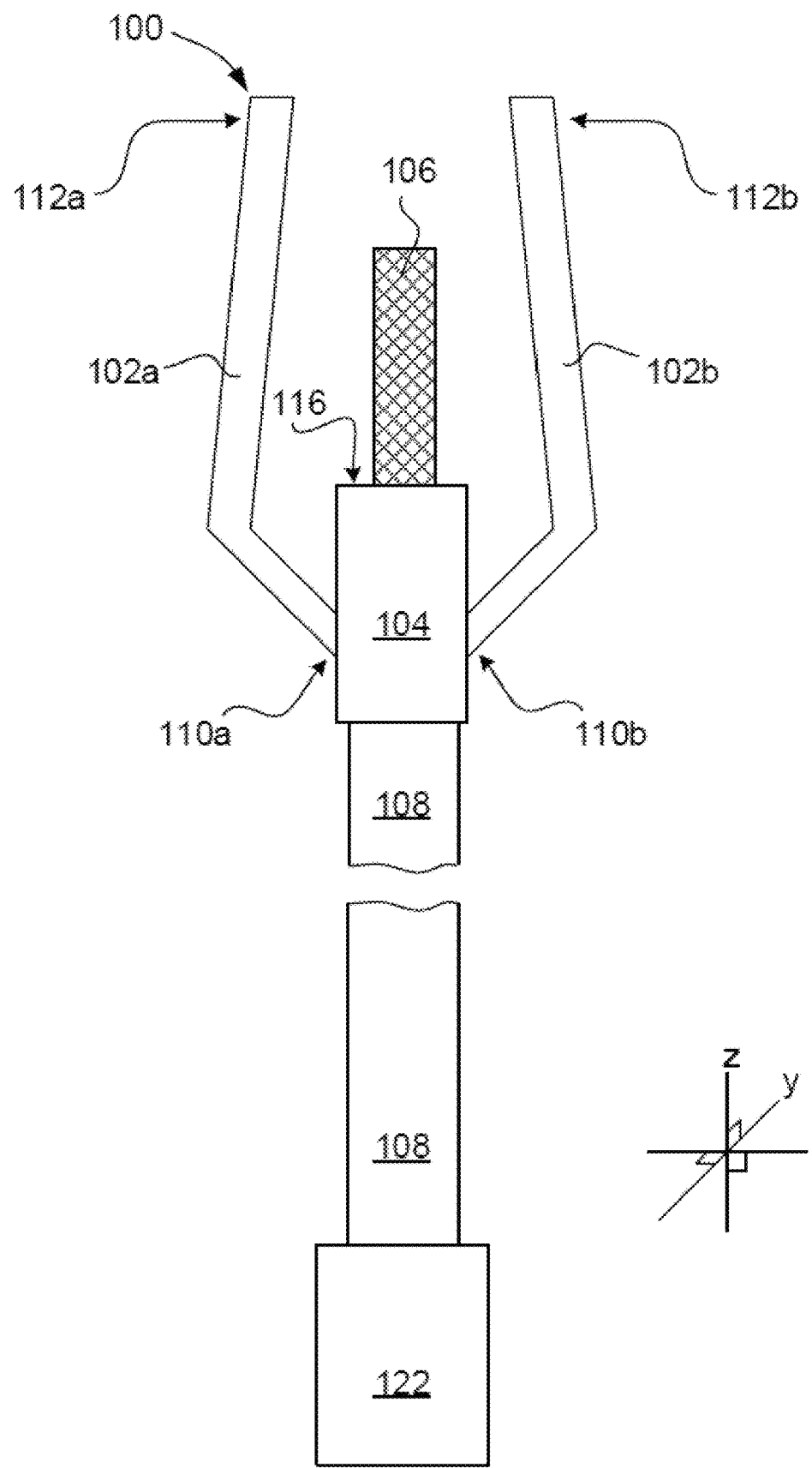
FIG. 6 is a side view of the delivery device of FIGS. 1A-1D, wherein the arm portion thereof is coupled to an optional handle, according to one embodiment.

In various embodiments, the arm 108 comprises a handle 122 located opposite to the end coupled to the capsule 104, as shown in the exemplary embodiment of FIG. 6. The handle 122 comprises a suitable shape and size to enable a physician or other medical professional to grip said handle 122 by hand and guide the arm 108 through the desired areas of a patient's heart. The handle 122 can also comprise one or more power buttons (not shown in FIG. 6) that can be actuated in an on/off position to control the dispensing of the adhesive 118 via the applicator 106, to control the function (e.g., the power on/off) of the energy elements 120, to control the actuation of the capture features or paddles 102a, 102b, and/or to control the function of any other component operatively coupled to the delivery device 100.

In some embodiments the capsule 104, arm 108, and optional handle 122 have substantially the same width as one another, while in some embodiments, the width of the arm 108 is less than the width of the capsule 104 and/or the handle 122.

In some embodiments, the capsule 104, arm 108, and/or optional handle 122 represent portions/parts of a single, continuous structure. In some embodiments, the arm 108 is a separate component than the capsule 104 and/or the optional handle 122.

In some embodiments, the capsule 104, arm 108, and/or optional handle 122 can each comprise one or more internal cavities/lumens. In some embodiments, one or more internal cavities/lumens can extend throughout the capsule 104, arm 108, and/or optional handle 122. These interior cavities can be concentric, arranged side-by-side, or a combination thereof.

Figure 7:
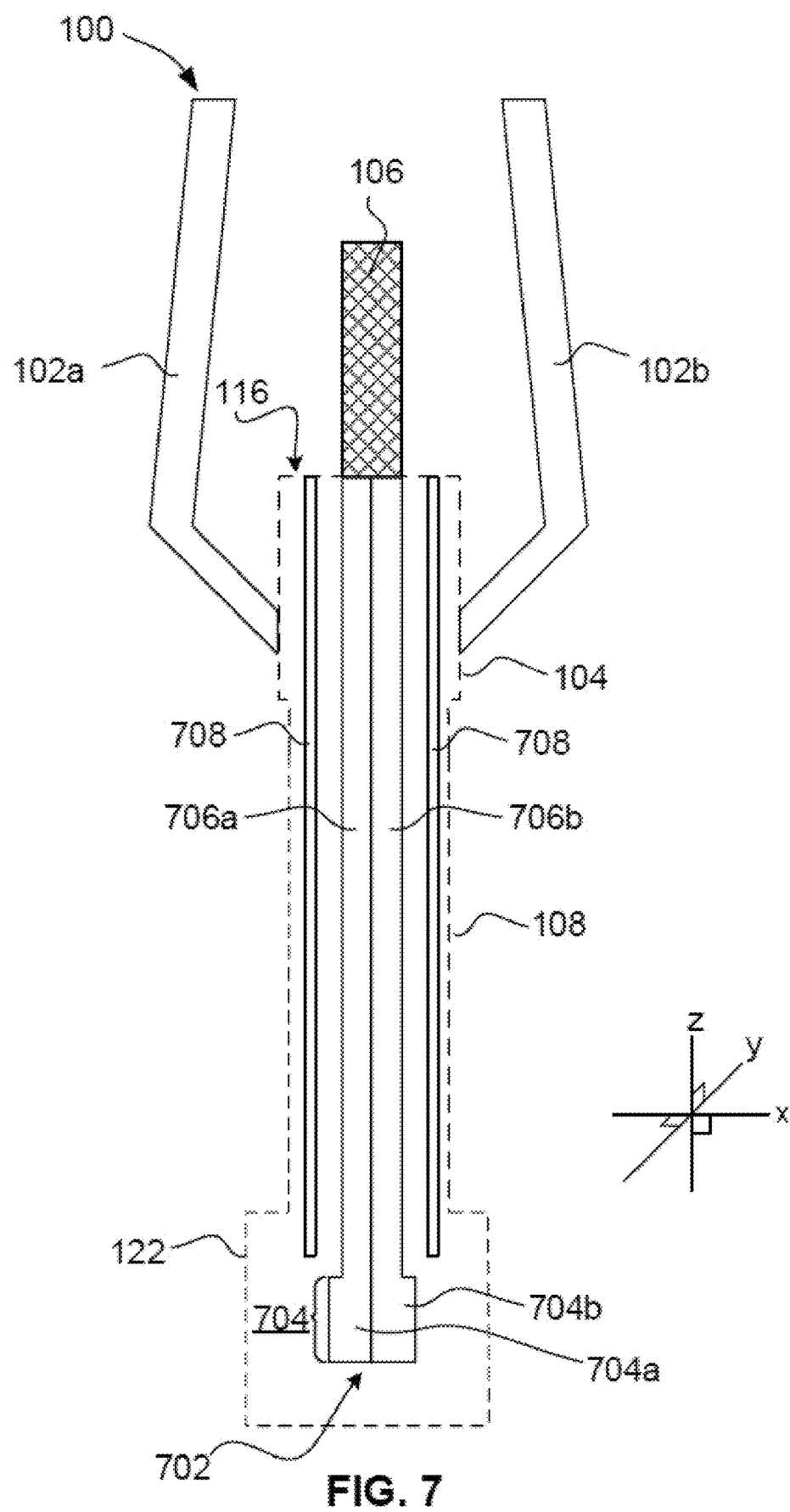
FIG. 7 is a side view of the delivery device of FIGS. 1A-1D illustrating one or more interior cavities/lumens thereof, according to one embodiment.

FIG. 7 illustrates an exemplary configuration of one or more interior cavities/lumens present within, and extending throughout, the capsule 104, arm 108, and optional handle 122. For clarity, the periphery of the capsule 104, arm 108, and optional handle 122 is indicated by a dotted line. It should be noted that FIG. 7 is for exemplary purposes only and describes various features that may be incorporated into embodiments of this disclosure.

As particularly shown in FIG. 7, an adhesive delivery assembly 702 is provided in one such interior cavity/lumen. This adhesive delivery assembly 702 can comprise a cartridge 704 that contains the adhesive. In some embodiments, the cartridge 704 comprises two chambers 704a, 704b, with one chamber comprising a pre-polymer as discussed herein, and the other chamber comprising an initiator as discussed herein. In some embodiments, the cartridge 704 is also in fluidic communication with the applicator 106, and thus able to supply/feed the adhesive thereto. For instance, the adhesive delivery assembly 702 can comprise one or more channels 706a, 706b configured to transport the pre-polymer and initiator, respectively from the cartridge 704 to the applicator 106. While the cartridge 704 can be housed in the optional handle 122 of the delivery device 100, as shown in FIG. 7, in some embodiments, the cartridge 704 can be housed in a portion of the arm 108 or the capsule 104.

Transfer of the adhesive contained within the aforementioned cartridge 704 to the applicator 106 can be achieved via various means. In some embodiments, the cartridge 704 is coupled to a piston mechanism (e.g., a plunger) configured to reduce the volume (and thereby increase the pressure) within the cartridge 704, thereby forcing the adhesive from the cartridge 704 towards and into the applicator 106. The piston mechanism can be activated electronically (e.g., via a power button present on the optional handle 122 or the arm 108) or mechanically.

In some embodiments, the cartridge 704 is coupled to a source of compressed gas or air, which, when activated, provides compressed gas or air to the cartridge 704 to force the adhesive towards and into the applicator 106. In various embodiments, a power button (e.g., on the optional handle 122 or the arm 108), is actuated in an on/off position to control the generation of compressed air into the cartridge. In such embodiments, a pressure regulator (e.g., coupled to the cartridge 704 and/or the source of compressed air) is used to regulate the amount of pressure applied to the cartridge 704 to force the adhesive out of the cartridge and towards and into the applicator 106. It is of note, however, that the adhesive can be supplied to the applicator 106 via other means as would be appreciated by skilled artisans upon reading the present disclosure.

As also shown in FIG. 7, the delivery device 100 comprises connection means 708 (e.g., electrical conductors/wires, wireless connection, RFID, etc.) to operatively couple the energy elements 120 to an energy/power source. The connection means 708 can be housed in an interior cavity/lumen extending from the capsule 104, arm 108, and/or the optional handle 122. In some embodiments, the energy sources 120 is coupled, via the connection means, to a power button present on the optional handle 122 or the arm 108.

In embodiments in which at least one of the energy elements 120 is configured to provide electromagnetic radiation, said energy element can be fiber optic. In some embodiments, this fiber optic extends from the upper surface 116 of the capsule 104 through the arm 108 (and the optional handle 122 if present).

Additionally, the delivery device 100 can comprise an actuation system, parts of which can be present within an interior cavity/lumen of the capsule 104, arm 108, and/or the optional handle 122. In some embodiments, the actuation system is coupled, and configured, to actuate the capture features or paddles 102a, 102b. The actuation system can comprise any suitable actuation element or elements such as gears, shafts, pulleys, screws, nuts, spindles, axles, wheels, etc. The actuation system can also comprise an electric actuator (e.g., a motor such as a DC brushed, brushless motor, AC motor, servo motor, stepped motor, etc.), a hydraulic actuator, pneumatic actuator, and/or a mechanical actuator, etc. In some embodiments, a single actuation system (and motor) is configured to actuate each of the capture features (e.g., both of the paddles 102a, 102b). In some embodiments, each of the capture features or paddles 102a, 102b is independently actuated via separate actuation systems (and, e.g., respective motors, pulleys, etc.). For instance, in one embodiment, each of the capture features or paddles 102a, 102b is actuated between the open and closed configurations by one or more servo motors, allowing for precise linear and/or rotational motion. An example of an actuation system for use in transcatheter delivery is illustrated and described in Pat. Pub. No.: US 2017/0231756 A1, of which the portions relevant to actuation are incorporated herein by reference.

Further, connection means (e.g., electrical conductors/wires) can operatively couple the capture features or paddles 102a, 102b and the actuation system to an energy/power source. The connection means can be housed in an interior cavity extending from the capsule 104 and through the arm 108 (and the optional handle 122 if present). In some embodiments, the capture features or paddles 102a, 102b and actuation system can be coupled, via the connection means, to a power button present on the optional handle 122 or the arm 108.

It is of note that the delivery device 100, and the components thereof, are not limited to the configuration shown in FIGS. 1A-1D to FIG. 7. For example, FIGS. 8-15 illustrate variations of the delivery device 100 as shown, e.g., in FIGS. 1A-1D to FIG. 7, where the same or similar components and features are given the same reference number. It is of note that the devices/components/features described in FIGS. 8-15 can be implemented in combination with or as an alternative to the devices/components/features described herein, such as those described with reference to other embodiments and figures. The delivery devices of FIGS. 8-15 can additionally be utilized in any of the methods of making and/or using such devices described herein.

Figure 8:
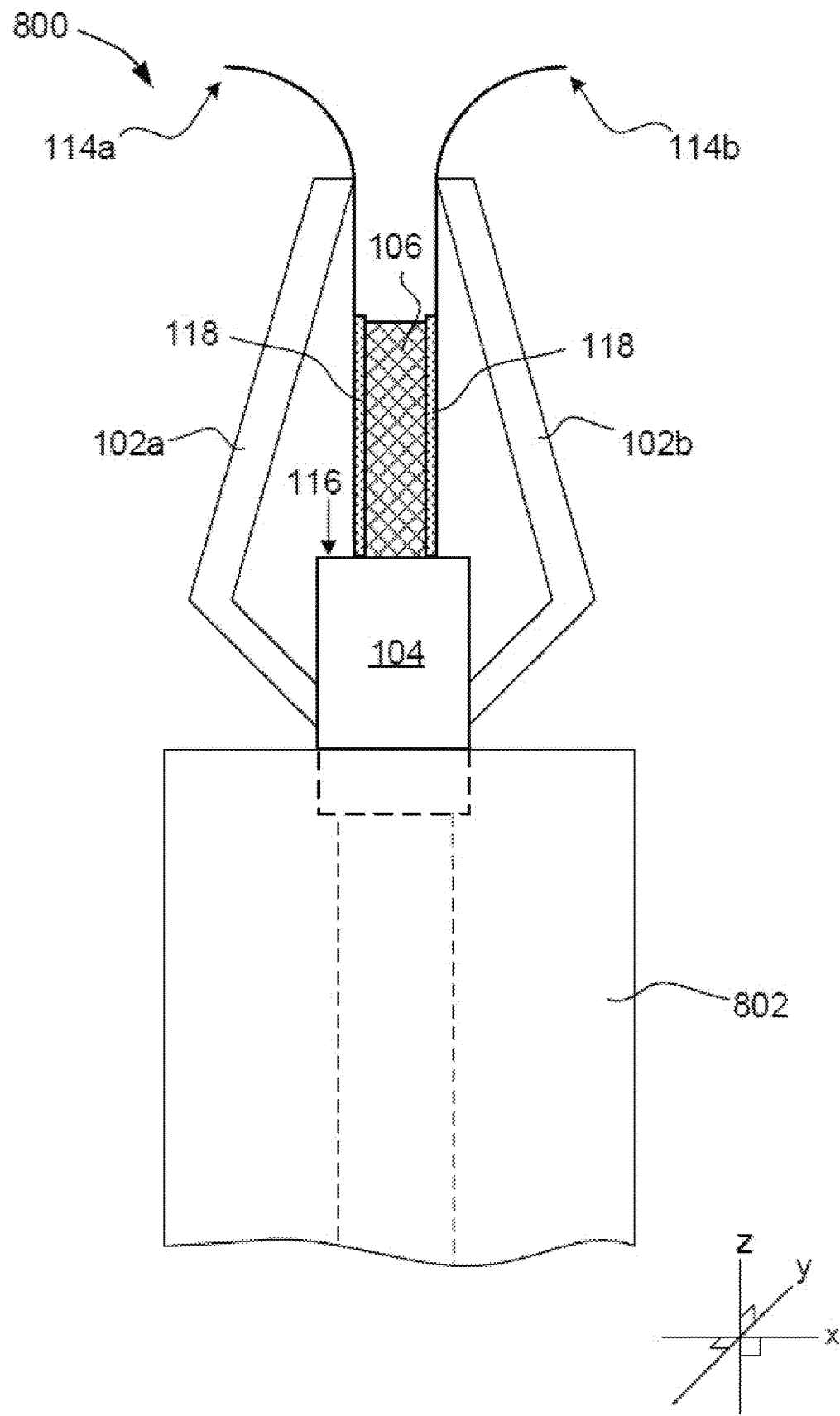
FIG. 8 is a side view of the delivery device of FIGS. 1A-1D illustrating a delivery sheath to cover and/or protect a delivery device, according to one embodiment.

As shown in the embodiment of FIG. 8, the delivery device 800 comprises a delivery sheath 802 (delivery catheter). In embodiments including a delivery sheath 802, the delivery sheath 802 is dimensioned to enable the capture features or paddles 102a, 102b (either in the open or closed configuration), the capsule 104, and the applicator 106 to retract therein. In some embodiments, the delivery sheath 802 extends (e.g., lengthwise) along at least a portion of the arm 108, while in some embodiments, the delivery sheath 802 will extend the full length of the arm 108.

The incorporation of the delivery sheath 802 may be advantageous for the transport of the delivery device 800 through the heart. For instance, during insertion of the delivery device 800 within a patient, the capture features or paddles 102a, 102b (either in the open or closed configuration), the capsule 104, and the applicator 106 can be present within an interior cavity/lumen of the delivery sheath 802. Once the delivery device 800 is introduced into the heart (e.g., the left ventricle) and positioned near the native leaflets (e.g., mitral leaflets 114a, 114b), the capture features or paddles 102a, 102b (either in the open or closed configuration), the capsule 104, and the applicator 106 can be extended from the delivery sheath 802. As discussed previously, the capture features or paddles 102a, 102b can then be actuated so as to capture the leaflets (e.g., 114a, 114b) and draw said leaflets together so as to allow application of the adhesive 118 therebetween via the applicator 106. After application of the adhesive and/or curing of the adhesive via the energy elements 120, the capture features or paddles 102a, 102b, the capsule 104, and the applicator 106 (if not detached) can again be retracted within the delivery sheath 802 to allow easy withdrawal of the delivery device 800 from the patient.

As shown in the embodiment of FIG. 9, in some embodiments, the delivery device 900 comprises capture features or paddles 102a, 102b having attachment portions 110a, 110b coupled to the upper surface (the first end) 116 of the capsule 104, with the applicator 106 positioned therebetween. As illustrated in FIG. 9, some embodiments will dimension the capsule 104 to enable the capture features or paddles 102a, 102b (either in the open or closed configuration), and the applicator 106 (if not-detachable) to retract therein. In some embodiments, the delivery device 900 comprises a delivery sheath having an interior cavity dimensioned so at allow the capture features or paddles 102a, 102b (either in the open or closed configuration), the capsule 104, and the applicator 106 to retract therein, as discussed with reference to FIG. 8.

FIGS. 10-14 illustrate embodiments in which the capture features (e.g., paddles) of a delivery system have different overall shapes and/or widths as otherwise described herein. For instance, as shown in the side view of FIG. 10, the delivery system 1000 can comprise capture features or paddles 1002a, 1002b that each extend in a substantially linear fashion from the attachment portions 1004a, 1004b to the end portions 1006a, 1006b thereof. The capture features or paddles 1002a, 1002b of delivery device 1000 do not comprise the different angled segments of the capture features or paddles 102a, 102b of delivery device 100 (see, e.g., FIGS. 1A-1D). In various embodiments, linear capture features or paddles 1002a, 1002b of delivery device 1000 are attached to a side portion of the capsule 104, as shown for example in FIG. 10. In some embodiments, linear capture features or paddles 1002a, 1002b of delivery device 1000 are attached to the upper surface 116 of the capsule 104, as described with reference to FIG. 9. In some embodiments, the delivery device 1000 is also used in conjunction with a delivery sheath 802, as described with reference to FIG. 8.

Figure 11:
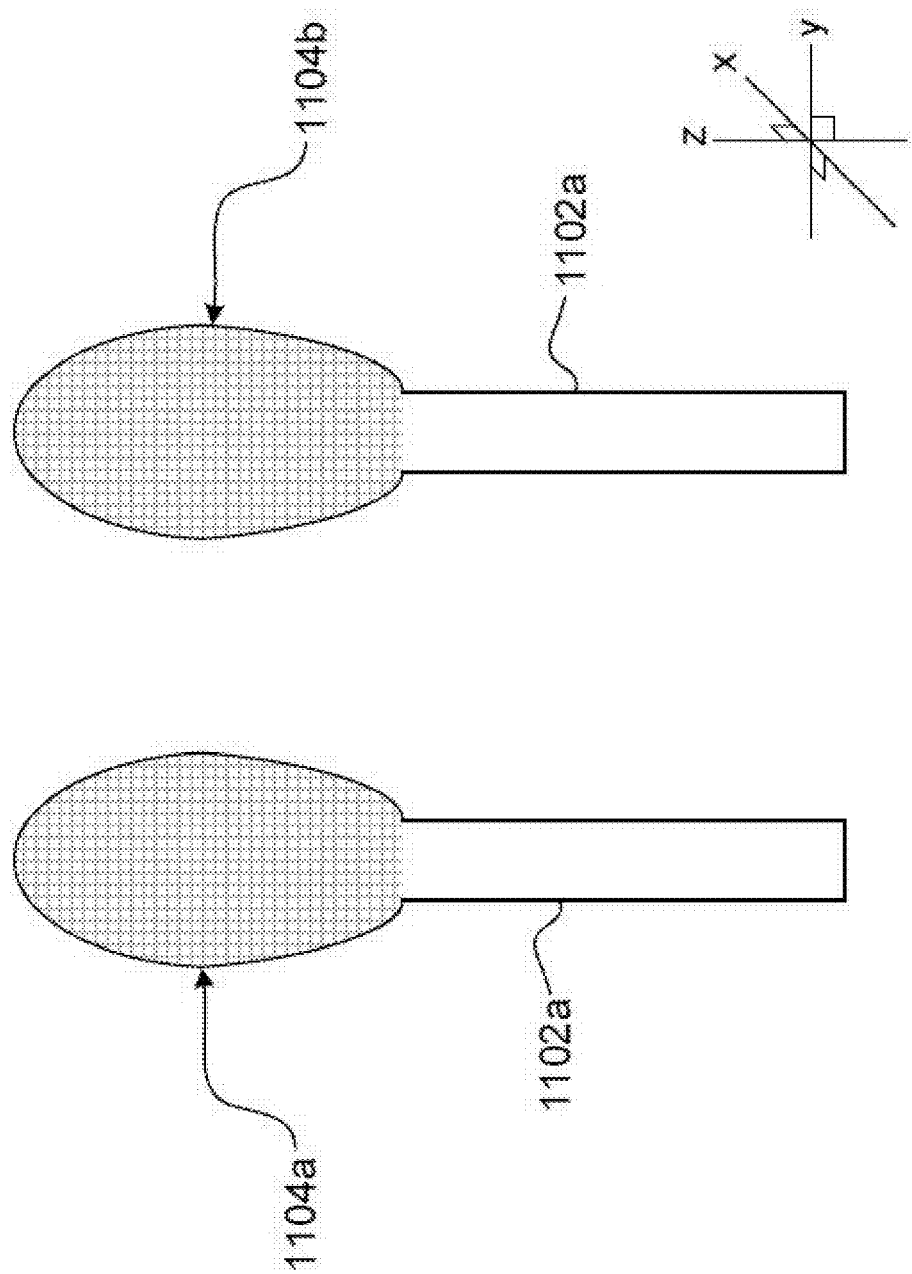
FIG. 11 is a front view of an exemplary pair of paddles configured to capture leaflets (e.g., anterior and posterior mitral leaflets), according to one embodiment.

As shown in the exemplary embodiment of FIG. 11, some embodiments of a delivery system (e.g., delivery system 100), include capture features or paddles 1102a, 1102b having a non-uniform width extending along the lengthwise direction. For clarity, the accompanying delivery device is absent in FIG. 11, and the interior surface of the capture features or paddles 1102a, 1102b (i.e., the surface that will face and contact the native leaflets or mitral leaflets) is shown. As illustrated in FIG. 11, the end portions 1104a, 1104b of each of the capture features or paddles 1102a, 1102b can have a substantially rounded shape. In some embodiments, the end portions 1104a, 1104b of each of the capture features or paddles 1102a, 1102b possess means to aid in contacting and/or gripping native valve leaflets (e.g., 114a, 114b). Such means include, but are not limited to, a textured surface and/or a coating. Textured surfaces can include ridges, hatches, or any pattern that may aid in and/or increase efficacy of gripping native valve leaflets. Coatings can include a temporary and/or weak adhesive that can grip the native valve leaflets temporarily with minimal or no damage to native tissue. Additionally, the rounded end portions 1104a, 1104b of each of the capture features or paddles 1102a, 1102b of some embodiments are comprised of cloth or a woven mesh. It is of note that the end portions 1104a, 1104b of each of the capture features or paddles 1102a, 1102b are not limited to a rounded shape, and can comprise any shape configured for convenient capture of a native leaflet or mitral leaflet as would be appreciated by skilled artisans upon reading the present disclosure.

Figure 12:
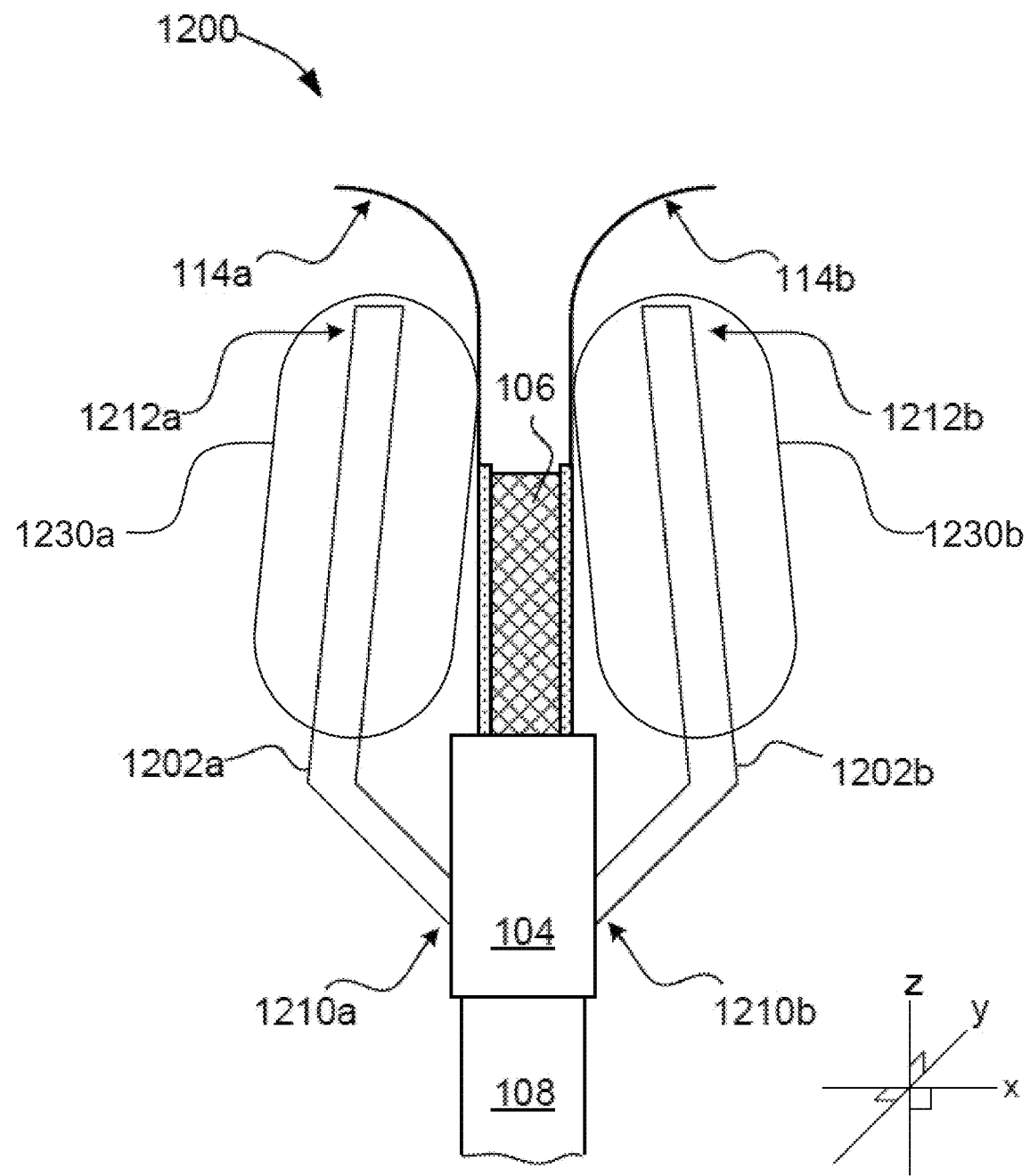
FIG. 12 is a side view of an exemplary delivery device with inflatable balloons utilized to capture native valve leaflets, according to one embodiment.

Turning now to FIG. 12, an illustration of one embodiment of a delivery device is described. In the embodiment of FIG. 12, inflatable balloons 1230a, 1230b are utilized to capture native valve leaflets 114a, 114b rather than using mechanical opening and closing of capture features or paddles 1202a, 1202b. In embodiments utilizing inflatable balloons 1230a, 1230b, an inflation fluid will be pumped into the inflatable balloons 1230a, 1230b to narrow the distance between end portions 1212a, 1212b. In this way, the inflatable balloons 1230a, 1230b will press the leaflets 114a, 114b to contact applicator 106, which will allow an adhesive 118 to contact the leaflets 114a, 114b. Using inflatable balloons 1230a, 1230b may be beneficial, where mechanical movements, such as through joints (see FIG. 1C and accompanying text) may have issues, such as contamination, wear, and/or other limitations for use in the field of valve repair.

Figure 13A:
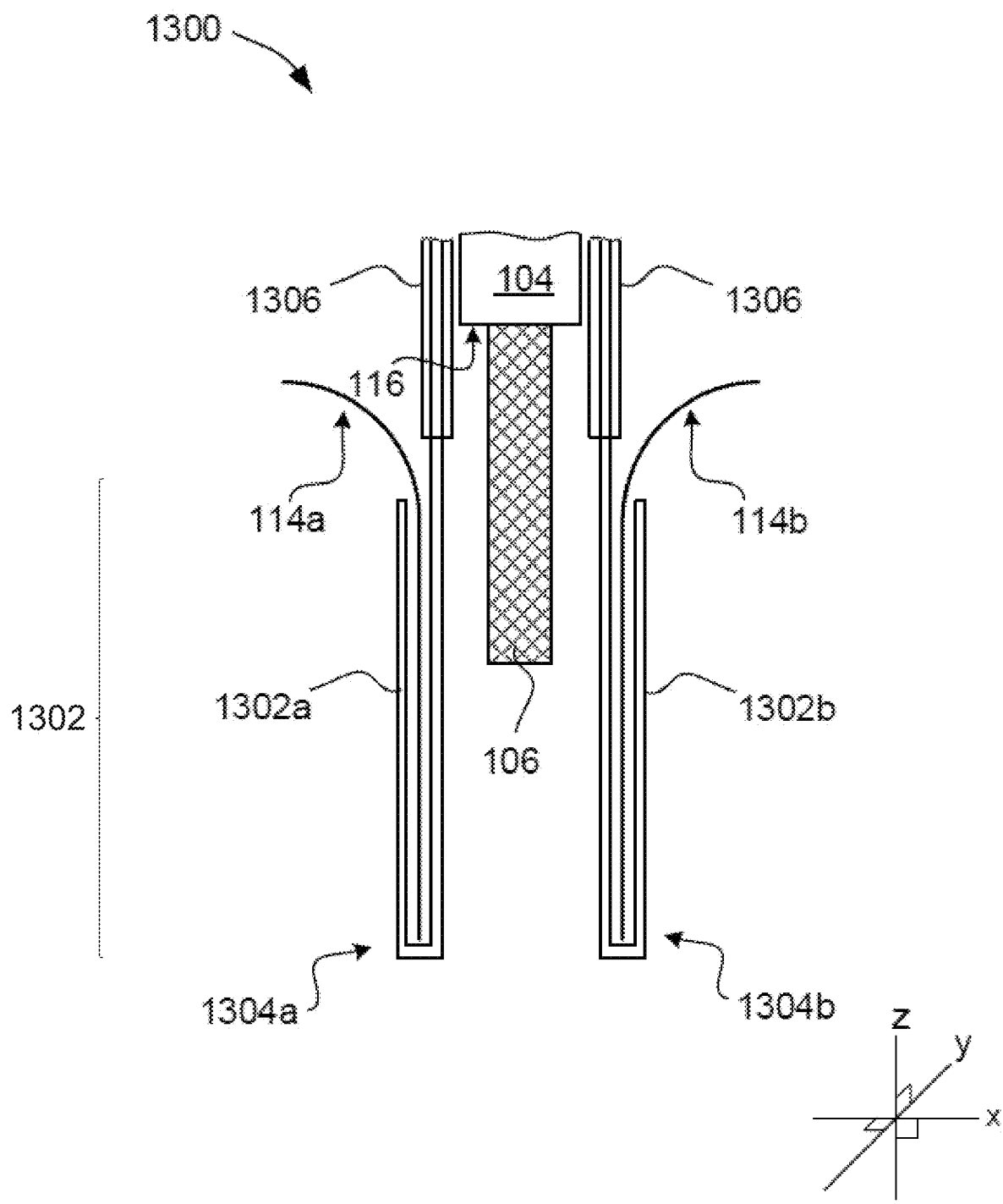
FIGS. 13A-13B are side and interior views, respectively, of an exemplary delivery device (e.g., a left atrial delivery device) for the localized fusion of native leaflets (e.g., mitral leaflets) via a biocompatible adhesive, according to one embodiment.
Figure 13B:
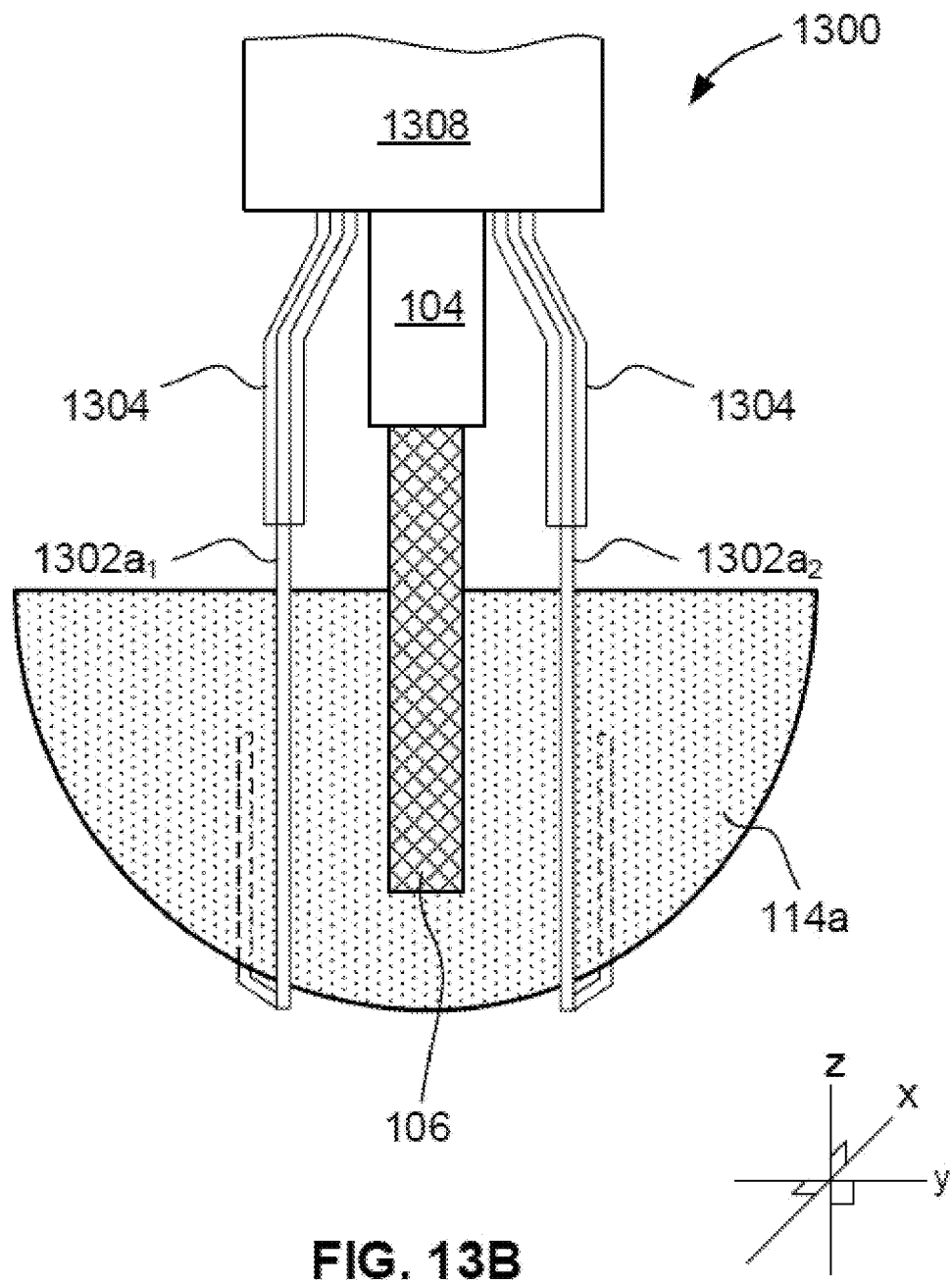

Referring now to FIGS. 13A-13B, a delivery device 1300 configured for the application of an adhesive between the posterior and anterior leaflets of a mitral valve is shown in accordance with one embodiment. The delivery device 1300 can include features similar to those described previously. However, while the delivery devices described in the preceding figures are configured such that left ventricle delivery/transport is facilitated, the delivery device 1300 of FIGS. 13A-13B is configured for transvascular and transseptal left atrial delivery. It is of note that the delivery device 1300 and the components/features thereof described in FIGS. 13A-13B can be implemented in combination with or as an alternative to the devices/components/features described herein, such as those described with reference to other embodiments and figures. It is of further note that like components and features are assigned the same reference number. The delivery device 1300 can also be used in various applications and/or in permutations, which may or may not be noted in the illustrative embodiments described herein. For instance, the delivery device 1300 can include more or less features/components than those shown in FIGS. 13A-13B, in some embodiments. Moreover, the delivery device 1300 is not limited to the size, shape, number of components, etc. specifically shown in FIGS. 13A-13B.

As shown in the side view of FIG. 13A, the delivery device 1300 comprises a capture feature 1302 for capturing native leaflets, for example, the anterior and posterior mitral leaflets 114a, 114b. In some embodiments, each capture feature 1302 comprises a pair of paddles 1302a, 1302b, with each paddle comprising at least two clips configured to contact, capture (e.g., "hook"), and move a native leaflet or mitral valve leaflet. For instance, FIG. 13B provides an interior view of anterior mitral leaflet 114a as captured ("hooked") by clips $1302a_1$ and $1302a_2$ of paddle 1302a (note paddle 1302b and its associated clips are not shown for clarity). In various embodiments, the clips of each paddle 1302a, 1302b is particularly dimensioned/shaped to capture a mitral valve leaflet. For instance, as shown in the embodiment of FIGS. 13A-13B, each clip can be substantially U-shaped.

In some embodiments, the paddles 1302a, 1302b can move from an open configuration to a closed configuration. In an open configuration, the end portions 1304a, 1304b of each paddle 1302a, 1302b are separated by a first distance. In some embodiments, this first distance corresponds to the maximum distance at which the end portions 1304a, 1304b of the paddles 1302a, 1302b can be separated from one another. In some embodiments, this first distance is sufficient to enable the paddles 1302a, 1302b to contact and capture the anterior and posterior mitral leaflets 114a, 114b.

In the closed configuration, the end portions 1304a, 1304b of each paddle 1302a, 1302b are separated by a second distance that is less than the aforementioned first distance. In some embodiments, this second distance is the minimum distance at which the end portions 1304a, 1304b of the paddles 1302a, 1302b can be separated from one another. In some embodiments, separation of the end portions 1304a, 1304b of the paddles 1302a, 1302b by this second distance results in the end portions being in contact, or in close proximity to, one another.

In some embodiments, the paddles 1302a, 1302b when positioned in the left atrial cavity of the heart, are in the open configuration to contact and capture the anterior and posterior mitral leaflets 114a, 114b, and then moved to the closed configuration to draw/move the leaflets 114a, 114b together so as to apply an adhesive therebetween. In instances in which the anterior and posterior leaflets 114a, 114b need to be readjusted with respect to the delivery device 1300, the paddles 1302a, 1302b can be opened and closed until the optimal position and/or coaptation depth is achieved.

Further, in various embodiments, the paddles 1302a, 1302b are configured to move in various directions and/or rotate independently of the other capture features or paddles 1302a, 1302b, such as described in relation to FIGS. 1A-1D. For instance, in some embodiments, each of the paddles 1302a, 1302b can be independently configured to move at least in a direction parallel with the x-axis and/or the y-axis as shown in FIGS. 13A-13B. In some embodiments, each of the paddles 1302a, 1302b are also independently able to rotate a predetermined amount about the y axis.

In some embodiments, paddle 1302a moves independently from paddle 1302b. However, in some embodiments, the two paddles 1302a, 1302b move in concert such that motion of one of the paddles causes, results in, and/or is associated with mirrored motion of the other paddle.

In some embodiments, each of the clips of the paddles 1302a, 1302b move interpedently from one another. For instance, in one embodiment, the delivery device 1300 do not include paddles, but rather include other capture features, e.g., four individual clips that can be independently steered so as to capture a portion of a mitral leaflet.

In various embodiments, movement and/or rotation of the capture features or paddles 1302a, 1302b, and/or individual clips, is achieved via various mechanical means, such as disclosed herein with reference to FIGS. 1A-1D to FIG. 7. For instance, in some embodiments, each of the capture features or paddles 1302a, 1302b, or each individual clip, is coupled to a portion of the delivery system via a joint that allows for the movement and/or rotation of said components.

As also shown in FIGS. 13A-13B, the delivery device 1300 comprises an applicator 106 extending from the upper surface (the first end) 116 of the capsule 104. As disclosed herein with reference to various embodiments, such applicator 106 is particularly configured to be positioned/inserted between native leaflets (e.g., between the anterior and posterior mitral leaflets 114a, 114b) captured between the capture features or paddles 1302a, 1302b. Further, the applicator 106 can be configured to dispense/apply an adhesive between the captured leaflets or the anterior and posterior mitral leaflets 114a, 114b. To that end, the capture features or paddles 1302a, 1302b can be moved to a closed configuration such that sidewalls of the applicator 106 contact and/or are in close proximity to at least a portion of the captured leaflets or mitral leaflets 114a, 114b, thereby enabling an adhesive to be directly applied to said portions of the leaflets 114a, 114b via the applicator 106 in various embodiments. In some embodiments, the adhesive is applied, via the applicator 106, to the middle segment (e.g., the A2-P2 segment) of the mitral leaflets 114a, 114b.

In some embodiments, the applicator 106 is detachable from the capsule 104. In some embodiments, the applicator 106 is configured to retract partially or completely within the capsule 104.

Moreover, in various embodiments, the delivery device 1300 additionally comprises one or more curing elements or energy elements (such as in FIG. 1D) configured to cure the adhesive dispensed from the applicator 106 and applied between the native leaflets or anterior and posterior mitral leaflets 114a, 114b. In some embodiments, the one or more energy elements can be positioned on one or more portions of the upper surface (the first end) 116 of the capsule 104. In one exemplary embodiment, a plurality of energy elements is located on the upper surface 116 of the capsule 104, and substantially surround and/or are spaced at equidistant locations around the base of the applicator 106.

In various embodiments, the delivery device 1300 comprise an arm coupled to a second end of the capsule 104 (such as illustrated in FIGS. 1A-1C). In some embodiments, the capture features or paddles 1302a, 1302b are attached to at least a portion of this arm, or to at least a portion of the capsule 104.

Further details and embodiments describing the configuration, materials, and function of the applicator 106, the adhesive dispensed therefrom, the capsule 104, the energy elements, the arm, and the interior cavities/lumens associated with any of the foregoing are described with reference to the delivery devices 100, 800, 900, 1000, and 1400 of FIGS. 1A-1D to FIG. 10 and FIG. 14 can be incorporated in the delivery device 1300 of FIGS. 13A-13B.

As shown in FIGS. 13A-13B, various embodiments of the delivery device 1300 include a microcatheter 1306 to encapsulate at least a portion of each capture feature or paddle 1302a, 1302b.

As additionally shown in FIG. 13B, some embodiments of the delivery device 1300 also include a deliver sheath/catheter 1308. In such embodiments, this delivery sheath 1308 is dimensioned to enable the capture features or paddles 1302a, 1302b (either in the open or closed configuration), the capsule 104, and the applicator 106 to retract therein. The delivery sheath 1308 can extend (e.g., lengthwise) along at least a portion or the full length of the arm of the delivery device 1300.

The incorporation of the delivery sheath 1308 can be advantageous for the transport of the delivery device 1300 through the heart. For instance, during insertion of the delivery device 1300 within a patient, the capture features or paddles 1302a, 1302b, the capsule 104, and the applicator 106 can be present within an interior cavity/lumen of the delivery sheath 1308. Once the delivery device 1300 is introduced into the left atrial cavity and positioned near the mitral leaflets 114a, 114b, the clips of the paddles 1302a, 1302b can be extended from the delivery sheath 1308 into the mitral valve toward the left ventricle and actuated to capture the mitral leaflets and form a "pocket" via the four clips. The capsule 104 and the applicator 106 can also be extended from the delivery sheath 1308 to allow application of the adhesive to the captured mitral leaflets via the applicator 106, and the subsequent curing of the applied adhesive via the energy elements located on the capsule 104. Once the adhesive is cured, the paddles 1302a, 1302b, the capsule 104, and the applicator 106 (if not detached) can again be retracted within the delivery sheath 1308 to allow easy withdrawal of the delivery device 1300 from the patient. Similar steps and features can be used for applying adhesive to other native valves.

Figure 14:
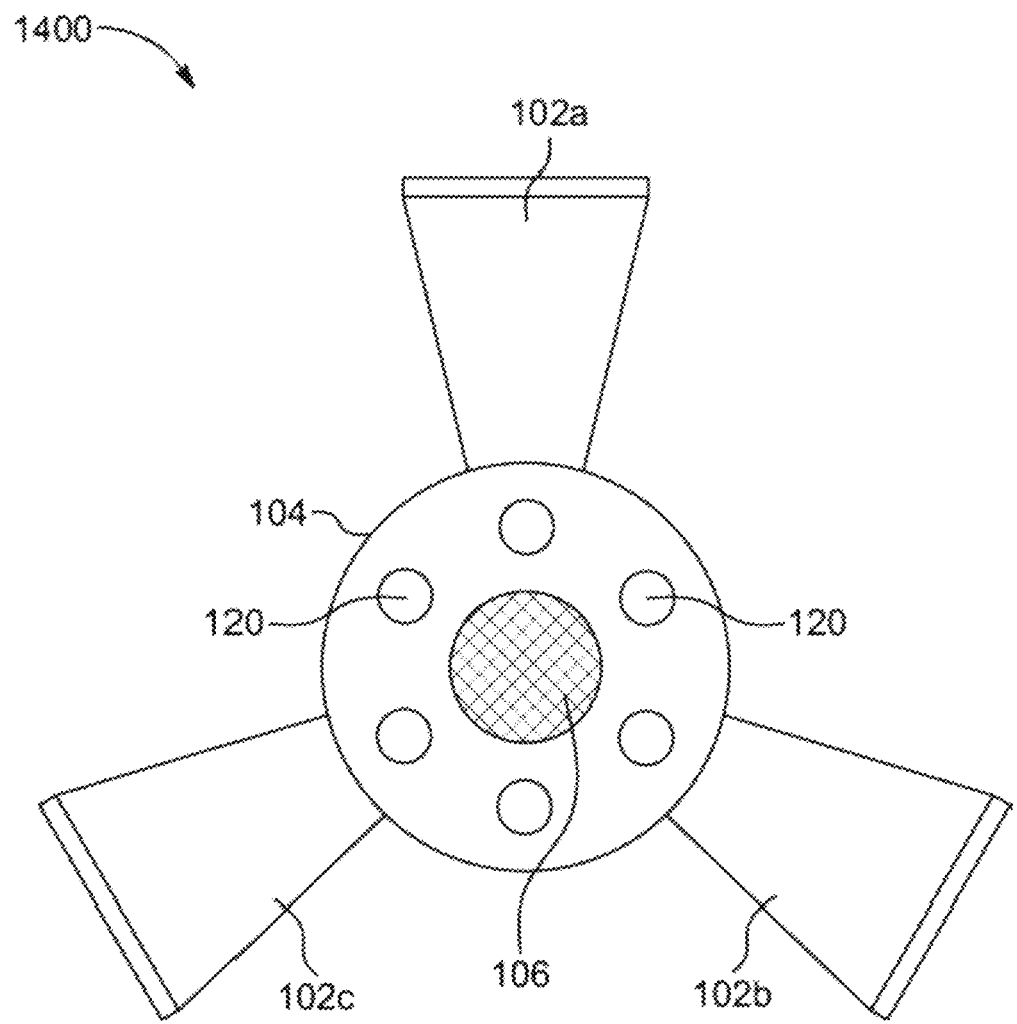
FIG. 14 is a top down view of a delivery device illustrating an exemplary 3-paddle configuration, according to one embodiment.

Turning now to FIG. 14, an embodiment of a delivery device 1400 comprising three capture features or paddles 102a, 102b, 102c is illustrated in a top-down view. Embodiments with a 3-paddle configuration can be used for native valves comprising 3 leaflets, such as the aortic valve, tricuspid valve, and/or pulmonic valve. In some embodiments, the three capture features or paddles 102a, 102b, 102c are attached to a capsule 104 with an applicator 106 and energy elements 120 arranged on the capsule 104, much in same way as described in FIG. 1D. In various embodiments, the delivery device 1400 is maneuvered, altered, and/or manipulated similarly to the configurations illustrated in FIGS. 1A-1D, such that the capture features or paddles 102a, 102b, 102c can operate simultaneously, where each capture feature or paddle moves in a mirrored fashion to the other two capture features or paddles. For example, manipulating capture feature or paddle 102a to an open position also manipulates capture features or paddles 102b and 102c to move to open positions. In some embodiments, each capture feature or paddle moves independently from the other two capture features or paddles. For example, manipulating capture feature or paddle 102a to an open position will have no effect on the position or state of capture features or paddles 102b and 102c.

Further details and embodiments describing the configuration, materials, and function of the applicator 106, the adhesive dispensed therefrom, the capsule 104, the energy elements, the arm, and the interior cavities/lumens associated with any of the foregoing are described with reference to the delivery devices 100, 800, 900, 1000, and 1300 of FIGS. 1A-1D to FIG. 13 can be incorporated in the delivery device 1400 of FIG. 14.

Figure 15A:
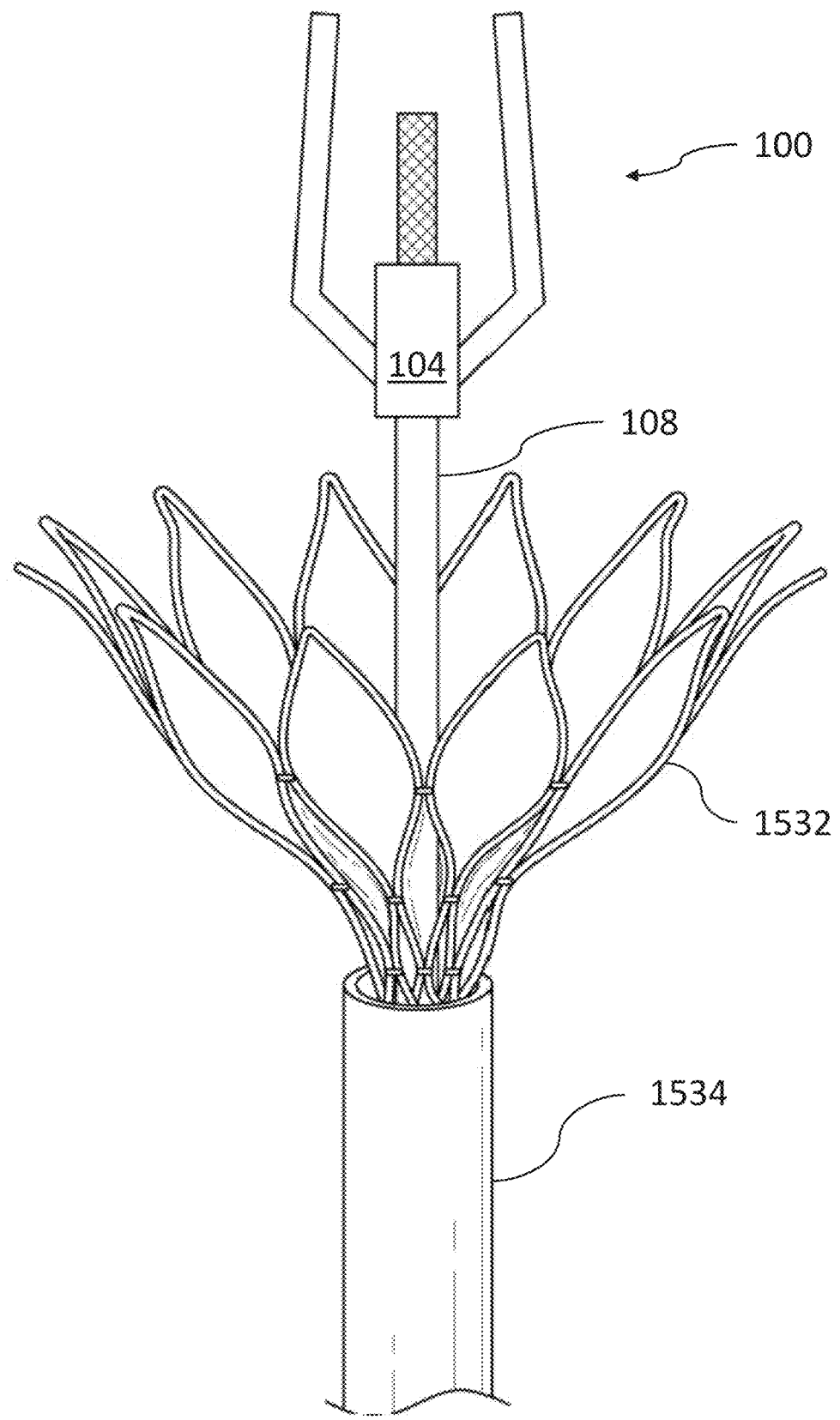
FIG. 15A is a side view of an exemplary delivery system including an expandable scaffold, according to one embodiment.
Figure 15B:
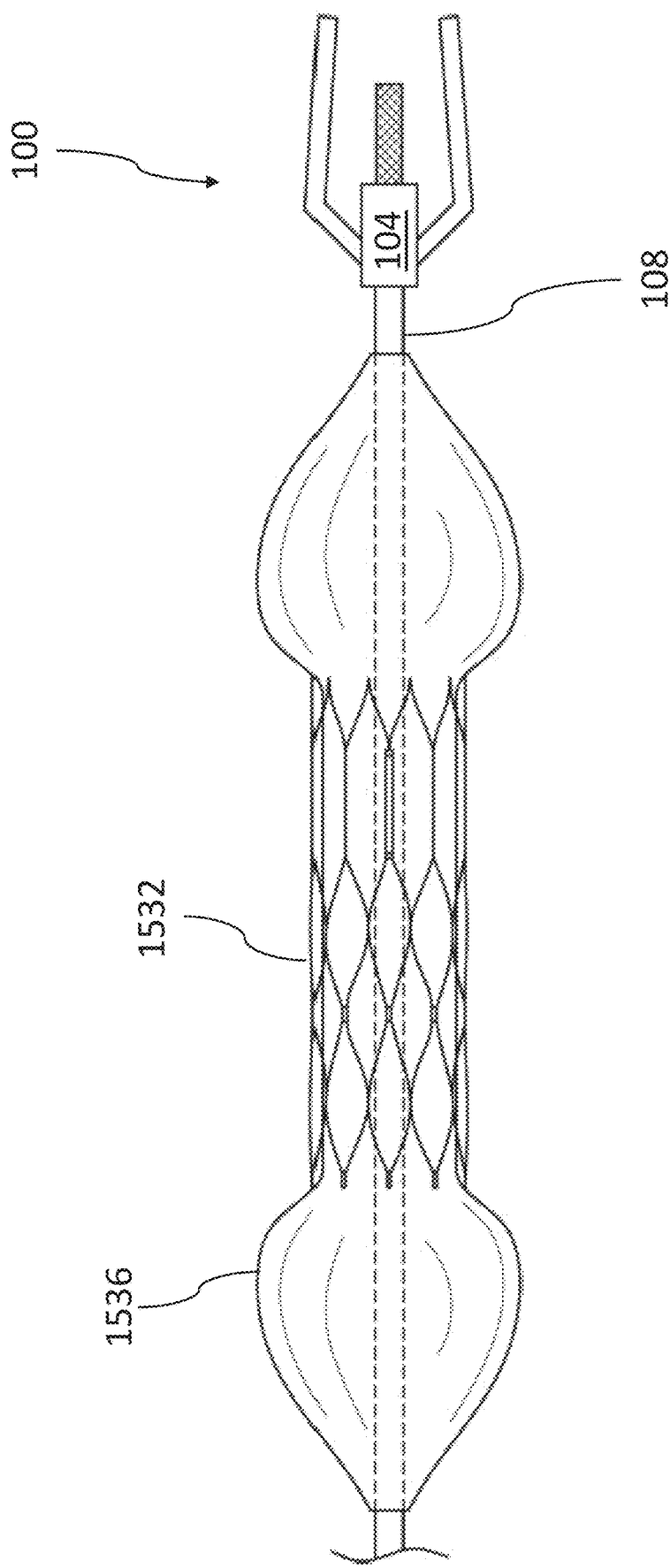
FIG. 15B is a side view of an exemplary delivery system including an expandable scaffold, where an inflatable balloon is used to expand the scaffold, according to one embodiment.

Turning now to FIGS. 15A-15B, some embodiments of the delivery device 100 include an expandable scaffold 1532. In the illustrated embodiment, the expandable scaffold 1532 is contained within a protective sheath 1534 as part of the arm 108 of the delivery device 100; however, some embodiments will have the expandable scaffold 1532 coupled to a portion of the capsule 104. In the embodiment of FIG. 15A, the protective sheath 1534 will either retract from the delivery device 100 or the arm 108 will extend from the protective sheath 1534 allowing the expandable scaffold 1532 to expand. In some embodiments, the protective sheath 1534 may not be present and other mechanical means may be used to expand the expandable scaffold 1532 from the arm 108 and/or capsule 104. In various embodiments, the protective sheath 1534 is the same as the delivery sheath 802 as described in relation to FIG. 8.

Turning now to FIG. 15B, one embodiment including an expandable scaffold 1532 is illustrated. In this embodiment, the expandable scaffold 1532 is disposed around an inflatable balloon 1536. In the illustrated embodiment, the expandable scaffold 1532 and inflatable balloon 1536 are assembled around part of the arm 108 of the delivery device 100; however, some embodiments will have the expandable scaffold 1532 coupled to a portion of the capsule 104. In embodiments including an inflatable balloon 1536, inflatable balloon 1536 will have a cavity that is in fluid communication with an interior cavity of the capsule 104 and/or the arm 108. Using this interior cavity, a suitable inflating fluid will be delivered to the inflatable balloon 1536 allowing the inflatable balloon 1536 to expand, thus causing expansion of the expandable scaffold 1532.

In embodiments comprising an expandable scaffold, such as illustrated in FIGS. 15A-15B, the expandable scaffold 1532 is radially expanded when the delivery device 100 is positioned in either the left ventricle or left atrium near the native leaflets (e.g., mitral leaflets 114a, 114b) so as to provide stability to the delivery device 100 during the capture of valve leaflets, application and/or delivery of the adhesive 118 therebetween, and/or curing of the adhesive 118. In various embodiments, the expandable scaffold 1532 is retractable to allow for easy withdrawal of the delivery device 100 from the patient.

Figure 16A:
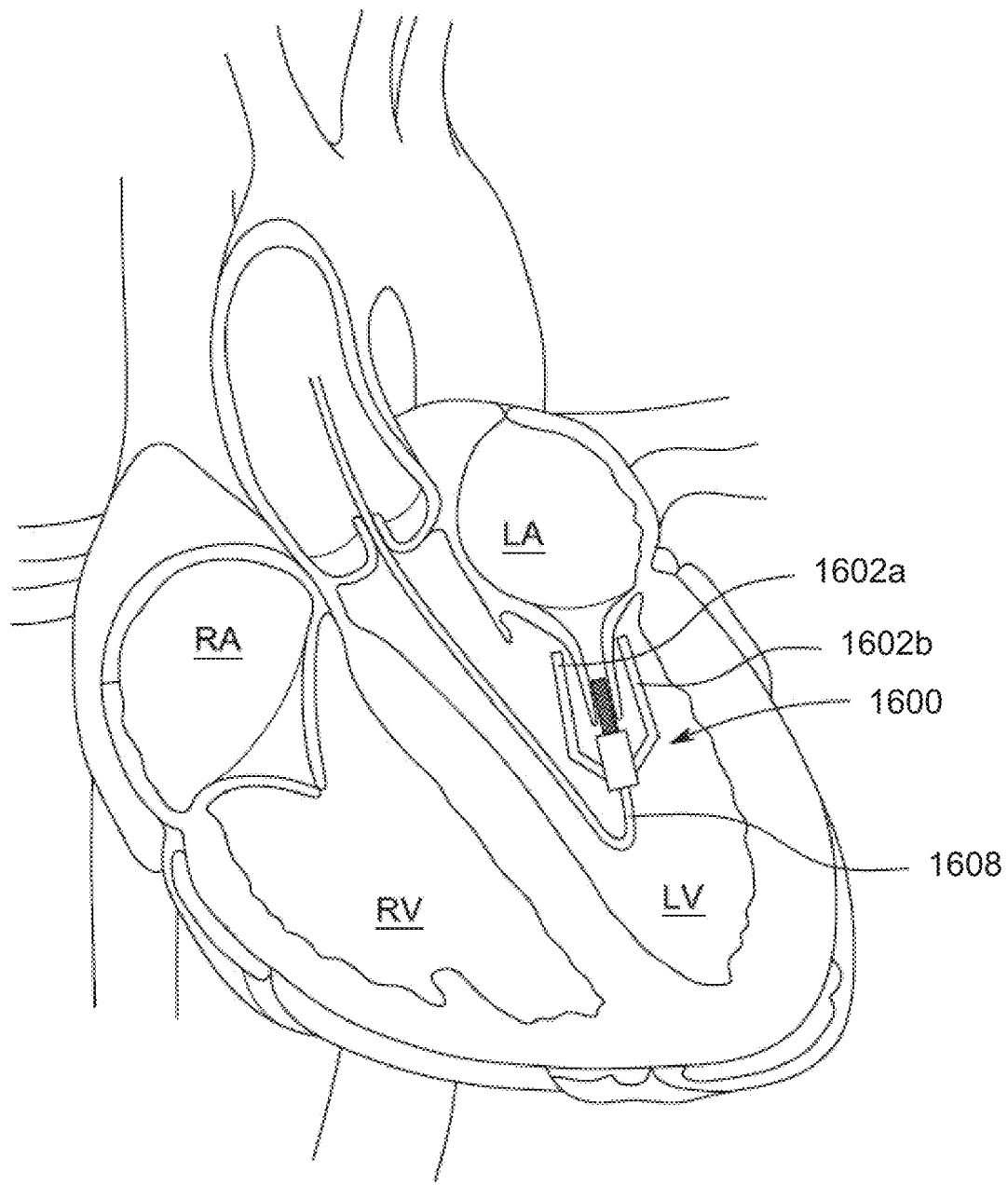
FIGS. 16A-16C illustrate an exemplary method for using a left ventricular delivery device as described herein, according to one embodiment.
Figure 16B:
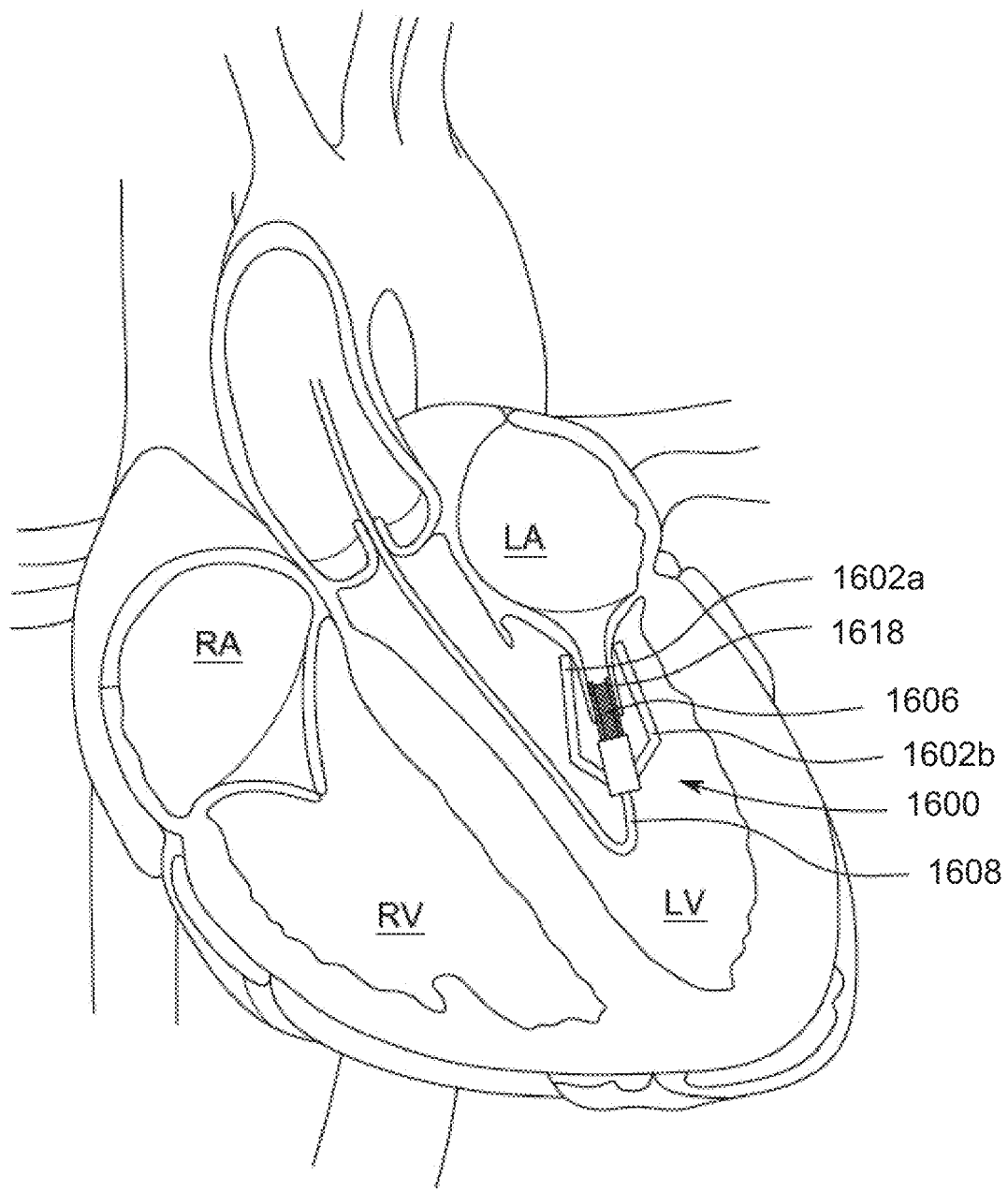
Figure 16C:
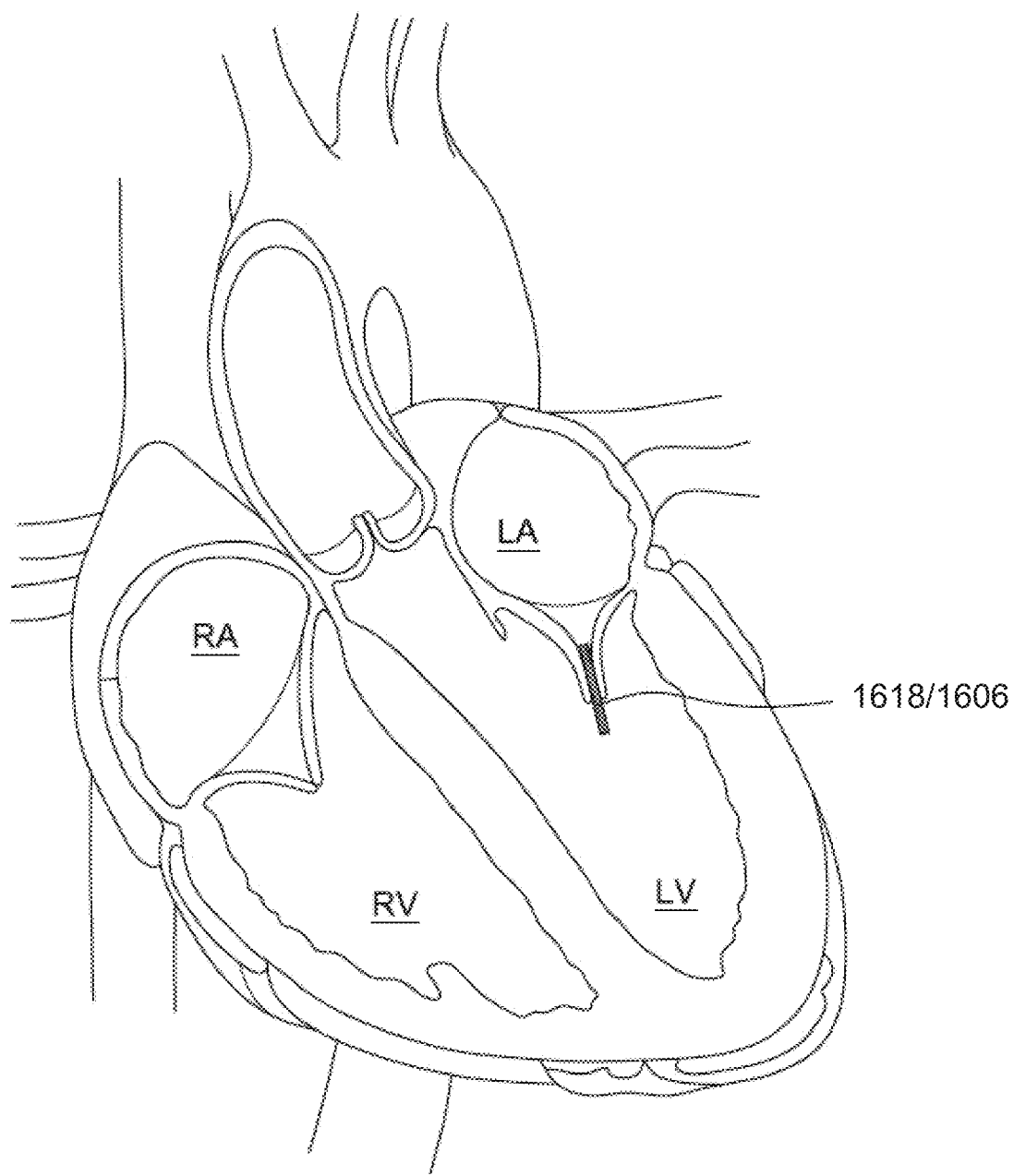

Referring now to FIGS. 16A-16C, an exemplary method of using a delivery device 1600, as described herein, is shown. While the method is generally illustrated with respect to the mitral valve, similar steps can be applied with respect to other native heart valves. As shown in FIG. 16A, the delivery device 1600 is advanced through the aorta into heart (e.g., through the left ventricle of the heart toward the left atrium) and positioned adjacent to the native leaflets (e.g., anterior and posterior mitral leaflets). The capture features (e.g., paddles 1602a, 1602b) are then opened to contact and capture the two or three native leaflets (e.g., mitral leaflets).

As illustrated in FIG. 16B, the capture features or paddles 1602a, 1602b are then moved to a closed configuration so as to draw the captured native leaflets (e.g., mitral leaflets) together to contact the applicator 1606. After contacting the applicator 1606 with the leaflets, adhesive 1618 is then dispensed between the captured leaflets via the applicator 1606. It is of note that, if the leaflets need to be readjusted prior to application of the adhesive 1618 thereto, the capture features or paddles 1602a, 1602b can be opened and closed until the optimal configuration and proper coaptation depth is achieved. After the adhesive 1618 is applied, the adhesive can be cured, e.g., with curing elements similar to those discussed previously.

Turning to FIG. 16C, after the adhesive 1618 is cured via the one or more curing or energy elements (e.g., a UV light source) associated with the delivery device 1600, the delivery device 1600 can be removed from the patient. At this stage, only the adhesive 1618 remains. However, in embodiments utilizing a detachable applicator, the applicator 1606 may also remain between the native leaflets.

Figure 17:
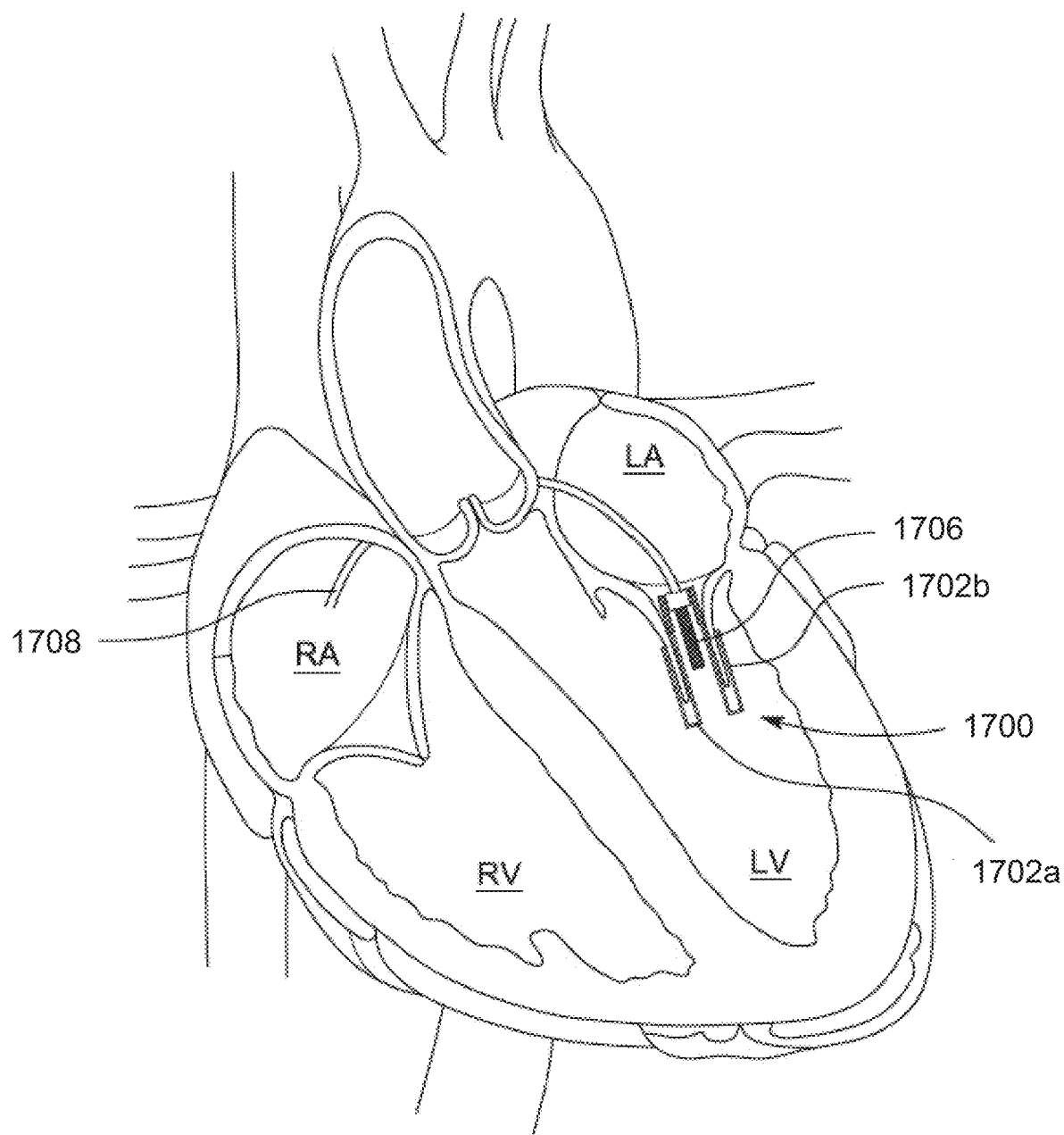
FIG. 17 illustrates an exemplary method for using a left atrial delivery device as described herein, according to one embodiment.

Turning now to FIG. 17, an exemplary method of using a delivery device 1700, as described herein, is shown. While the method is generally illustrated with respect to the mitral valve, similar steps can be applied with respect to other native heart valves. As shown in FIG. 17, the delivery device 1700 is advanced and positioned adjacent to the native leaflets (e.g., anterior and posterior mitral leaflets). To arrive at the left atrium as illustrated in FIG. 17, the delivery device 1700 is navigated to the right atrium and moved into the left atrium via a transseptal puncture. If treating the tricuspid valve, this can be done from the right atrium without requiring crossing the septum. Although numerous methods exist to position the delivery device in the right atrium, various embodiments will navigate the delivery device 1700 transvascularly (e.g., via the inferior vena cava, superior vena cava, a femoral vein, etc.). In one embodiment, the delivery device 1700 is navigated via transfemoral delivery, such that the delivery device 1700 is navigated through the femoral vein, through the inferior vena cava, and into the right atrium. If treating the mitral valve, a transseptal puncture can be performed and the delivery device 1700 passed through the transseptal puncture from the right atrium to the left atrium. In some embodiments, the delivery device 1700 is then passed from the atrium to the ventricle (e.g., the right atrium to the right ventricle or the left atrium to the left ventricle). Once arriving in the desired chamber of the heart or other desired location, the capture features (e.g., paddles 1702a, 1702b) are then opened to contact and capture the two or three native leaflets (e.g., mitral leaflets, tricuspid leaflets, etc.).

Similar to what is described in reference to FIG. 16B, the capture features or paddles 1702a, 1702b are then moved to a closed configuration so as to draw the captured native leaflets (e.g., mitral leaflets) together to contact the applicator 1706. After contacting the applicator 1706 with the leaflets, adhesive is then dispensed between the captured leaflets via the applicator 1606. It is of note that, if the leaflets need to be readjusted prior to application of the adhesive thereto, the capture features or paddles 1702a, 1702b can be opened and closed until the optimal configuration and proper coaptation depth is achieved. After the adhesive is applied, the adhesive can be cured, e.g., with curing elements similar to those discussed previously.

As described in relation to FIG. 16C, after the adhesive is cured via the one or more curing or energy elements (e.g., a UV light source) associated with the delivery device 1700, the delivery device 1700 can be removed from the patient. At this stage, only the adhesive and/or applicator remains.

After delivery of an adhesive via a delivery device as described herein, if residual valvular regurgitation or mitral regurgitation is present after the initial application of the adhesive to the native leaflets or mitral leaflets and the subsequent curing of the composition, additional applications of the adhesive can be applied at other locations along the native valve leaflets (e.g., adjacent to or spaced apart from the prior fusion site). This application can be repeated multiple times to achieve the desired regurgitation reduction (e.g., mitral regurgitation reduction).

Figure 18A:
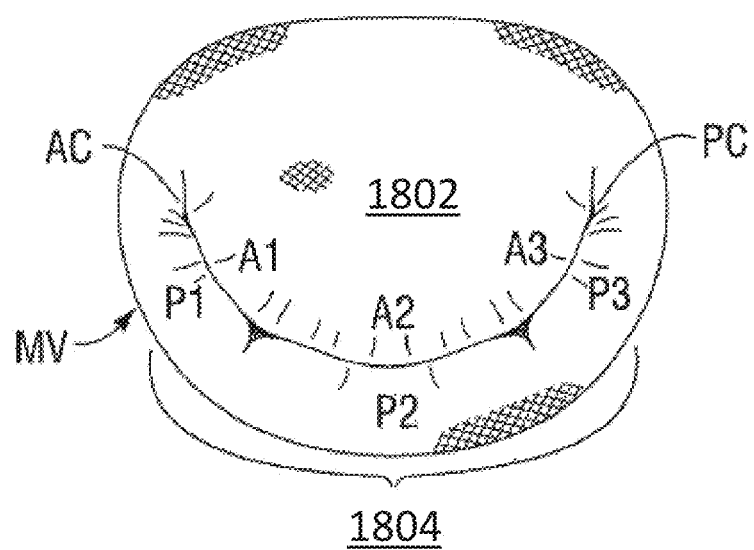
FIG. 18A illustrates a mitral valve according to Carpentier's definition.

Referring now to FIG. 18A, an illustration of Carpentier's definition of the mitral valve (MV) anatomy is shown. In FIG. 18A, anterior mitral leaflet 1802 and posterior mitral leaflet 1804 are illustrated with the various scallops of each of the mitral leaflets. In FIG. 18A, A2 and P2 represent the middle scallops of the anterior mitral leaflet 1802 and posterior mitral leaflet 1804, respectively. The lateral scallops (A1 and P1) and medial scallops (A3 and P3) are also labelled. AC and PC represent the anterolateral and posteromedial commissures of the mitral valve MV.

Figure 18B:
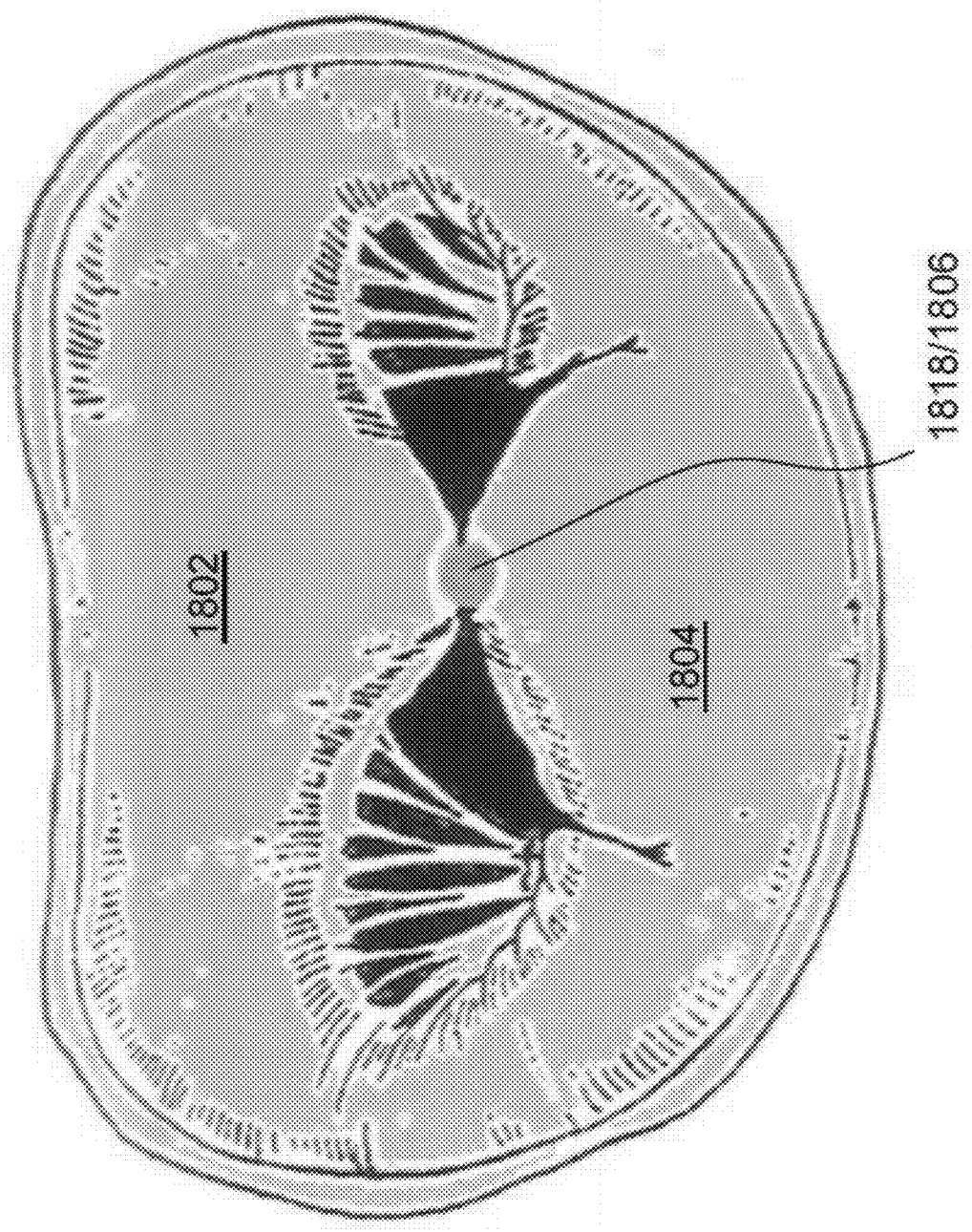
FIG. 18B illustrates a top down view of anterior and posterior mitral leaflets fused via a biocompatible adhesive such as can be applied via the devices, systems, and methods described herein.

Turning now to FIG. 18B, a top down view of anterior mitral leaflet 1802 and posterior mitral leaflet 1804 fused together via cured adhesive 1818 is shown. In some embodiments, the fusion is accomplished with the presence of a detachable applicator 1806. In some embodiments, the mitral leaflets 1802, 1804 are fused near the middle scallop of the leaflets, for example, at the A2-P2 segment of the leaflets per Carpentier's definition, as illustrated in FIG. 18A. However, depending on the disease etiology, the fusion of the leaflets can be applied anywhere along the coaptation front to restore the closing function of the valve.

In some embodiments, provided herein is a kit or delivery system comprising a delivery device as described herein, and a curable adhesive for use therewith. In some embodiments, the kit or delivery system further includes instructions on how to use the delivery device and/or curable adhesive.

Unless otherwise defined, all technical and scientific terms used herein have the same meaning as commonly understood by one of ordinary skill in the art of this invention.

Throughout the present specification and claims, unless the context requires otherwise, the word "comprise" and variations thereof (e.g., "comprises" and "comprising") are to be construed in an open, inclusive sense, that is as "including, but not limited to." Additionally, the singular forms "a," "an" and "the" include plural referents unless the context clearly dictates otherwise.

Recitation of numeric ranges of values throughout the specification is intended to serve as a shorthand notation of referring individually to each separate value falling within the range inclusive of the values defining the range, and each separate value is incorporated in the specification as it were individually recited herein.

Reference to "about" a value or parameter herein includes (and describes) embodiments that are directed to that value or parameter per se. In some embodiments, the term "about" includes the indicated amount±10%.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment, but may be in some instances. Furthermore, the particular features, structures, or characteristics may be combined in any suitable manner in one or more embodiments.

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications include the substitution of known equivalents for any aspect of the invention in order to achieve the same result in substantially the same way. The components and features of one embodiment can be combined with features and components of one embodiment, and steps described with respect to one method can be combined with other steps and/or incorporated into other methods described herein. Such modifications are also intended to fall within the scope of the appended claims.

What is claimed is:

1. A delivery device for application of an adhesive between anterior and posterior mitral leaflets for localized fusion thereof, the delivery device comprising:
   a capsule comprised of a first surface, a second surface, and at least one side surface, wherein the second surface is attached to an arm, wherein the first surface is opposite the second surface, and wherein the at least one side surface extending therebetween;
   one or more capture features comprising and end portion and an attachment portion, wherein the end portion is configured for capturing the anterior and posterior mitral leaflets and wherein the attachment portion is connected to the capsule or the arm;

an applicator configured to apply the adhesive directly to the captured anterior and posterior mitral leaflets and coupled to the first surface of the capsule;

a cartridge in fluid communication with the applicator and containing the adhesive;

one or more energy elements located on the first surface of the capsule and configured to cure the applied adhesive;

a handle attached to the arm on an end opposite of the capsule comprising controls to actuate the one or more capture features, to apply the adhesive, and to activate the one or more energy elements; and a delivery sheath extending along at least a portion of the arm and with dimensions to allow the capsule, one or more capture features, and applicator to retract therein.

2. The delivery device of claim 1, wherein at least one of the one or more energy elements is configured to deliver ultraviolet (UV) radiation to cure the applied adhesive.

3. The delivery device of claim 1, wherein at least one of the one or more energy elements is a fiber optic configured to deliver ultraviolet (UV) radiation out of a distal tip thereof.

4. The delivery device of claim 1, wherein the applicator is constructed of a fabric or polymeric material that is braided, woven, or formed into a sponge-like material.

5. The delivery device of claim 1, wherein the adhesive comprises at least one pre-polymer and at least one initiator.

6. The delivery device of claim 5, wherein the at least one pre-polymer is activated by one or more functional groups that can be reacted to form crosslinks between polymer chains and wherein the at least one pre-polymer is not activated by biological fluids.

7. The delivery device of claim 1, wherein the one or more capture features comprises a pair of opposing paddles, each paddle configured to articulate between an open and closed configuration to capture one of the anterior or posterior mitral leaflets.

8. The delivery device of claim 1, wherein the arm has a sufficient length to advance the capture features to the anterior and posterior mitral leaflets.

9. The delivery device of claim 1, wherein the one or more energy elements substantially surround the applicator.

10. The delivery device of claim 1, wherein the applicator is at least one of (i) detachable from the capsule and (ii) configured to retract within an interior cavity of the capsule.

11. The delivery device of claim 1, wherein the capsule comprises at least one interior cavity in fluid communication with the applicator, wherein the adhesive is stored in the at least one interior cavity prior to being applied between the anterior and posterior mitral leaflets via the applicator.

12. The delivery device of claim 1, further comprising an expandable scaffold coupled to at least a portion of the capsule or at least a portion of the arm, wherein the expandable scaffold is configured to stabilize the delivery device during application of the adhesive between the anterior and posterior mitral leaflets.

13. The delivery device of claim 1, wherein the one or more capture features comprises a pair of opposing paddles coupled to at least a portion of the capsule, wherein each paddle is configured to articulate between an open and closed configuration to capture one of the anterior or posterior mitral leaflets.

14. A method for localized fusion of anterior and posterior mitral leaflets via application of an adhesive therebetween, the method comprising:

positioning a delivery device according to claim 1 adjacent to at least the anterior leaflet and the posterior leaflet, separately capturing the anterior leaflet and the posterior leaflet via the capture means of the delivery device;

applying the adhesive directly to at least the anterior leaflet and posterior leaflet via the applicator of the delivery device; and after applying the adhesive, curing the adhesive via the at least one energy element of the delivery device to locally fuse at least the anterior leaflet and the posterior leaflet together.

15. The method of claim 14, wherein the applicator is constructed of a fabric or polymeric material that is braided, woven, or formed into a sponge-like material.

16. The delivery device of claim 1, wherein the applicator is detachable.

17. The delivery device of claim 16, wherein the applicator is constructed of a biodegradable or bioresorbable material.

18. The delivery device of claim 1, wherein the delivery sheath extends the entire length of the arm and is connected to the handle, wherein the handle further comprises controls to retract the capsule, the one or more capture features, and the applicator into the delivery sheath.

* * * * *